US010169539B2

(12) United States Patent
Reihman et al.

(10) Patent No.: US 10,169,539 B2
(45) Date of Patent: Jan. 1, 2019

(54) DATA BACKFILLING FOR CONTINUOUS GLUCOSE MONITORING

(71) Applicant: DexCom, Inc., San Diego, CA (US)

(72) Inventors: Eli Reihman, San Diego, CA (US); Sebastian Bohm, San Diego, CA (US); Leif N. Bowman, San Diego, CA (US); Katherine Yerre Koehler, Solana Beach, CA (US); Disha B. Sheth, Oceanside, CA (US); Peter C. Simpson, Cardiff, CA (US); Jim Stephen Amidei, Escondido, CA (US); Douglas William Burnette, San Diego, CA (US); Michael Robert Mensinger, San Diego, CA (US); Eric Cohen, San Diego, CA (US); Hari Hampapuram, San Diego, CA (US); Phil Mayou, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 273 days.

(21) Appl. No.: 15/287,581

(22) Filed: Oct. 6, 2016

(65) Prior Publication Data

US 2017/0124350 A1    May 4, 2017

Related U.S. Application Data

(63) Continuation of application No. 15/287,450, filed on Oct. 6, 2016, now Pat. No. 9,996,668.
(Continued)

(51) Int. Cl.
*G06F 19/00* (2018.01)
*G16H 40/63* (2018.01)
(Continued)

(52) U.S. Cl.
CPC ........ *G06F 19/3406* (2013.01); *A61B 5/0004* (2013.01); *A61B 5/14532* (2013.01);
(Continued)

(58) Field of Classification Search
CPC .... G16H 15/00; G16H 10/60; G09G 2370/16; G09G 2370/10; G06F 3/1415;
(Continued)

(56) References Cited

U.S. PATENT DOCUMENTS 6,687,546 B2    2/2004    Label et al.
7,344,500 B2    3/2008    Talbot et al.
(Continued)

*Primary Examiner* — Robert Craddock
(74) *Attorney, Agent, or Firm* — Knobbe Martens Olson & Bear, LLP

(57) ABSTRACT

Methods and apparatus, including computer program products, are provided for backfilling. In some example embodiments, there is provided a method that includes receiving, at a receiver, backfill data representative of sensor data stored, at a continuous blood glucose sensor and transmitter assembly, due to a loss of a wireless link between the receiver and the continuous blood glucose sensor and transmitter assembly; generating, at the receiver, at least one of a notification or a graphically distinct indicator for presentation at a display of the receiver, the at least one of the notification or the graphically distinct indicator enabling the backfill data to be graphically distinguished, when presented at the display, from non-backfill data; and generating, at the receiver, a view including the backfill data, the non-backfill data, and the generated at least one of the notification or the graphically distinct indicator. Related systems, methods, and articles of manufacture are also described.

13 Claims, 17 Drawing Sheets

Related U.S. Application Data

(60) Provisional application No. 62/269,480, filed on Dec. 18, 2015, provisional application No. 62/249,043, filed on Oct. 30, 2015.

(51) Int. Cl.
| | | |
|---|---|---|
| *A61B 5/00* | (2006.01) | |
| *A61B 5/145* | (2006.01) | |
| *G06F 21/62* | (2013.01) | |
| *G06F 3/14* | (2006.01) | |
| *G16H 10/60* | (2018.01) | |
| *G16H 15/00* | (2018.01) | |
| *G06T 11/00* | (2006.01) | |
| *G09G 5/377* | (2006.01) | |
| *G06T 11/20* | (2006.01) | |
| *H04W 12/06* | (2009.01) | |
| *G06F 17/30* | (2006.01) | |
| *H04W 12/02* | (2009.01) | |

(52) U.S. Cl.
CPC ............ *A61B 5/7275* (2013.01); *A61B 5/746* (2013.01); *G06F 3/1415* (2013.01); *G06F 19/3418* (2013.01); *G06F 21/6245* (2013.01); *G16H 10/60* (2018.01); *G16H 15/00* (2018.01); *G16H 40/63* (2018.01); *G06F 17/30867* (2013.01); *G06F 17/30979* (2013.01); *G06Q 2220/10* (2013.01); *G06T 11/001* (2013.01); *G06T 11/206* (2013.01); *G09G 5/377* (2013.01); *G09G 2354/00* (2013.01); *G09G 2370/10* (2013.01); *G09G 2370/16* (2013.01); *H04W 12/02* (2013.01); *H04W 12/06* (2013.01)

(58) Field of Classification Search
CPC ............ G06F 21/6245; G06F 17/30979; G06F 17/30867; G06F 19/3418; A61B 5/7275; A61B 5/746; A61B 5/14532; A61B 5/0004; H04W 12/02; H04W 12/06; G06Q 2220/10
See application file for complete search history.

(56) References Cited

U.S. PATENT DOCUMENTS

| | | |
|---|---|---|
| 7,811,231 B2 | 10/2010 | Jin et al. |
| 8,187,183 B2 | 5/2012 | Jin et al. |
| 8,542,122 B2 | 9/2013 | Goodnow et al. |
| 8,617,069 B2 | 12/2013 | Bernstein et al. |
| 8,622,903 B2 | 1/2014 | Jin et al. |
| 8,672,844 B2 | 3/2014 | Say et al. |
| 9,035,767 B2 | 5/2015 | Fennell et al. |
| 9,226,701 B2 | 1/2016 | Sloan et al. |
| 9,310,230 B2 | 4/2016 | Harper |

DATA BACKFILLING FOR CONTINUOUS GLUCOSE MONITORING

INCORPORATION BY REFERENCE TO RELATED APPLICATION

Any and all priority claims identified in the Application Data Sheet, or any correction thereto, are hereby incorporated by reference under 37 CFR 1.57. This application is a continuation of U.S. application Ser. No. 15/287,450, filed on Oct. 6, 2016, which claims the benefit of U.S. Provisional Appl. No. 62/249,043, filed on Oct. 30, 2015, and U.S. Provisional Appl. No. 62/269,480, filed on Dec. 18, 2015. Each of the aforementioned applications is incorporated by reference herein in its entirety, and is hereby expressly made a part of this specification.

FIELD

The present disclosure generally relates to continuous glucose monitoring.

BACKGROUND

Diabetes mellitus is a disorder in which the pancreas cannot create sufficient insulin. In a diabetic state, a person suffering from high blood sugar may experience an array of physiological side effects associated with the deterioration of small blood vessels. These side effects may include, for example, kidney failure, skin ulcers, bleeding into the vitreous of the eye, and the like. A hypoglycemic reaction, such as a low blood sugar event, may be induced by an inadvertent overdose of insulin, or after a normal dose of insulin or glucose-lowering agent. In a severe hypoglycemic reaction, there may be a high risk for headache, seizure, loss of consciousness, and coma.

A diabetic person may carry a self-monitoring blood glucose (SMBG) monitor which typically requires the user to prick his or her finger to measure his or her glucose levels. Given the inconvenience associated with traditional finger pricking methods, it is unlikely that a diabetic will take timely SMBG measurements and, consequently, may be unaware whether his or her blood glucose value is indicative of a dangerous situation.

Consequently, a variety of non-invasive, transdermal (e.g., transcutaneous) and/or implantable electrochemical sensors are being developed for detecting and/or quantifying blood glucose values. These devices generally transmit raw or minimally processed data for subsequent analysis at a remote device. The remote device may have a display that presents information to a user hosting the sensor. In some systems, a patient may check his or her glucose level on a hand held computing device. There are challenges to presenting this information discreetly and reliably.

SUMMARY

Methods and apparatus, including computer program products, are provided for determining backfilling data at a receiver of analyte data.

In some example embodiments, there is provided a method that includes receiving, at a receiver, backfill data representative of sensor data stored, at a continuous blood glucose sensor and transmitter assembly, due to a loss of a wireless link between the receiver and the continuous blood glucose sensor and transmitter assembly; generating, at the receiver, at least one of a notification or a graphically distinct indicator for presentation at a display of the receiver, the at least one of the notification or the graphically distinct indicator enabling the backfill data to be graphically distinguished, when presented at the display, from non-backfill data; and generating, at the receiver, a view including the backfill data, the non-backfill data, and the generated at least one of the notification or the graphically distinct indicator.

In some implementations, the above-noted aspects may further include additional features described herein including one or more of the following. The graphically distinct indicator may include a color that is different from another color used to present the non-backfill data. The graphically distinct indicator may include a symbol that is different from another symbol used to present the non-backfill data. The symbol may include at least one of a dashed line, a solid line, a solid polygon, or a hollow polygon. The graphically distinct indicator may include an overlay on the backfill data. The notification may include an indication that the non-backfill data is being presented at the display. The notification may indicate at least one alert occurring during a time associated with the backfill data. The notification may indicate a request to display the backfill data associated with a missed alert. The notification may indicate a request to consent to the display of the backfill data. The notification may indicate a request to consent to the display of the backfill data and at least one alert occurring during a time associated with the backfill data. The notification may indicate a request to display backfill data, when an alert is missed. The view may include a plot of glucose values formed from the backfill data and the non-backfill data. The receiver may display the view including the backfill data, the non-backfill data, and the generated at least one of the notification or the graphically distinct indicator. The backfill data may be displayed, when an indication of consent is received. The receiver may inhibit the receiving of the backfill data, without an indication of consent. The receiving may be in response to a request from the receiver. The receiver may classify an alert as a missed alert, when the alert occurred during a time associated with the backfill data.

In some example embodiments, there is provided a method that includes transmitting, by an analyte sensor system, at least one advertisement at a first time; receiving, at the analyte sensor system, a data connection request from a user equipment at a second time; establishing, by the analyte sensor system, the data connection with the user equipment; transmitting, by the analyte sensor system, an analyte value to the user equipment; storing, at the analyte sensor system, analyte data as backfill data, when an error occurs in the transmitting the at least one advertisement, the establishing the data connection, and/or the transmitting the analyte value; and transmitting, by the analyte sensor system, the stored backfill data.

In some implementations, the above-noted aspects may further include additional features described herein including one or more of the following. The stored backfill data may be transmitted, when another data connection is established to the user equipment. The stored backfill data may be transmitted via one or more other advertisements. Before the establishing of the data connection and/or the other data connection, an authentication may be performed. The analyte sensor system may store analyte data as backfill data, when an error occurs in the authenticating. The error may represent a state in which the transmitting the at least one advertisement, the establishing the data connection, the transmitting the analyte value, and/or the authenticating are not successful. The user equipment may include a mobile wireless device, a smart phone, a tablet, and/or a display device.

In some example embodiments, there is provided a method that includes receiving, by a user equipment, at least one advertisement at a first time from an analyte sensor system; transmitting, by the user equipment, a data connection request to the analyte sensor system at a second time; establishing the data connection with the analyte sensor system; receiving, by the user equipment, an analyte value from the analyte sensor system; and receiving, by the user equipment, backfill data stored at the analyte sensor system, when an error occurs.

In some implementations, the above-noted aspects may further include additional features described herein including one or more of the following. The stored backfill data may be received, when another data connection is established. The stored backfill data may be received via one or more other advertisements. Before the establishing of a data connection, an authentication may be performed. The error may represent a state in which the receiving the at least one advertisement, the transmitting the data connection request, the establishing the data connection, the receiving the analyte value, and/or the authentication are not successful. The user equipment may include a mobile wireless device, a smart phone, a tablet, and/or a display device.

In some example embodiments, there is provided a method that includes transmitting, by a user equipment, a data connection request to the analyte sensor system; establishing the data connection with the analyte sensor system; checking, by the user equipment, for private data stored at the user equipment and associated with the analyte sensor system, the private data encrypted to inhibit access by the user equipment; when the checking identifies private data associated with the analyte sensor system, requesting private data from the analyte sensor system; when the checking does not identify private data associated with the analyte sensor system, requesting, from the analyte sensor system, manifest data for the private data, and requesting, in response to receiving the manifest data, private data from the analyte sensor system; and receiving the requested private data to enable storage before forwarding to a server.

In some implementations, the above-noted aspects may further include additional features described herein including one or more of the following. The checking may further include querying a database to determine whether there is private data stored for the analyte sensor system. The requesting for private data may include a time frame over which the private data is requested. The time frame may be determined based on a time stamp obtained from private data stored in the database. The manifest data may describe the private data. The user equipment may include a mobile wireless device, a smart phone, a tablet, and/or a display device.

It is to be understood that both the foregoing general description and the following detailed description are exemplary and explanatory only and are not restrictive. Further features and/or variations may be provided in addition to those set forth herein. For example, the implementations described herein may be directed to various combinations and subcombinations of the disclosed features and/or combinations and subcombinations of several further features disclosed below in the detailed description.

BRIEF DESCRIPTION OF THE DRAWINGS

The accompanying drawings, which are incorporated herein and constitute a part of this specification, show certain aspects of the subject matter disclosed herein and, together with the description, help explain some of the principles associated with the subject matter disclosed herein. In the drawings.

Figure 1:
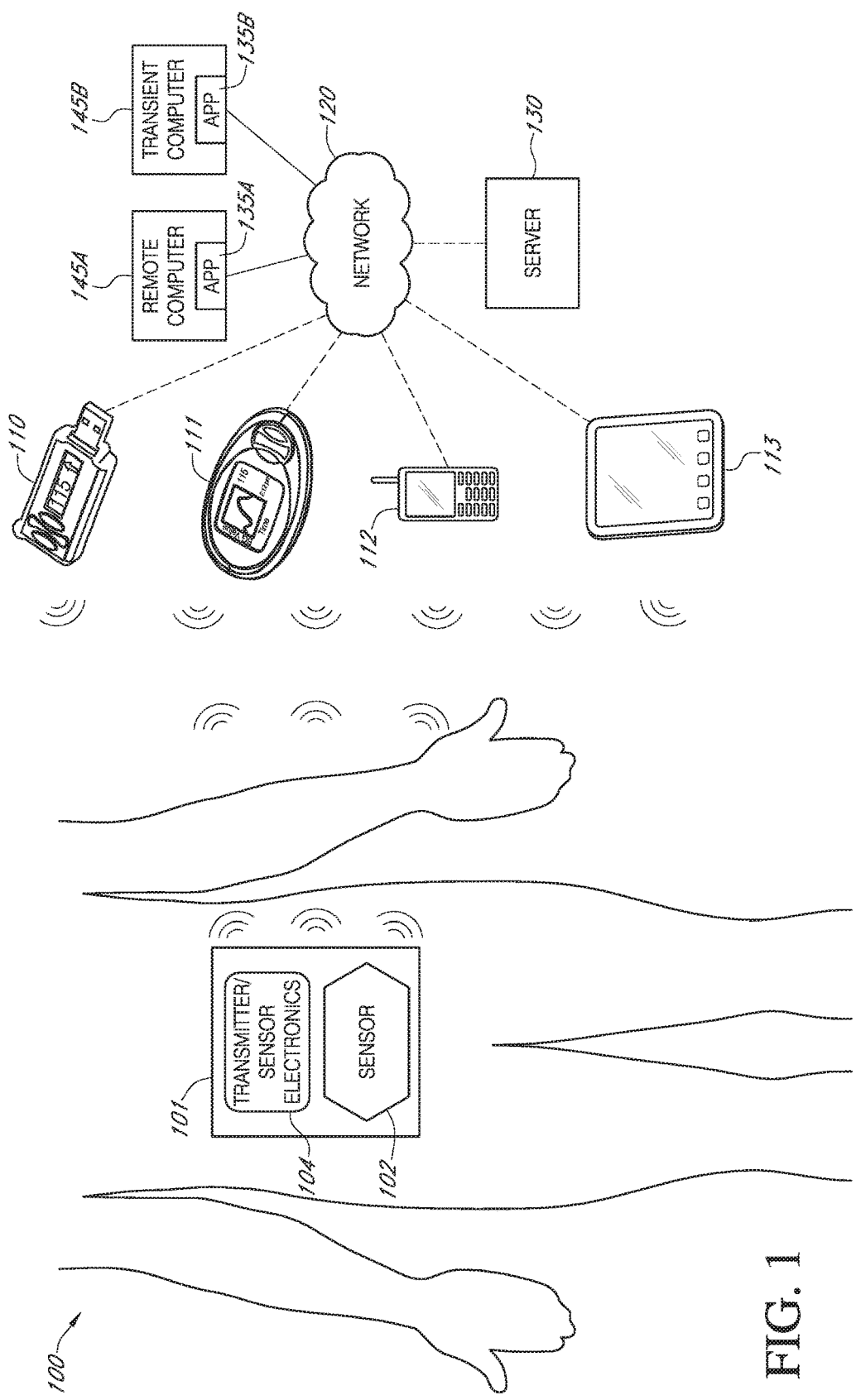
FIG. 1 illustrates a continuous analyte sensor system, in accordance with some example embodiments.

Like labels are used to refer to same or similar items in the drawings.

DETAILED DESCRIPTION

When the communication between a sensor, such as a sensor for estimating continuous glucose monitoring (CGM) values, and a receiver, such as a smartphone, tablet, or other processor-based display device, is interrupted due to a loss of a communication link between the sensor and receiver or some other error, the data packets wirelessly sent by the sensor to the receiver may be missed and thus not displayed by the receiver. While the communication link is unavailable, the sensor may store packets corresponding to analyte sensor measurements, such as CGM data. When communication is re-established, the sensor may be able to send the stored data as so-called "backfill" data to the receiver for display. However, this backfill data, although useful in some respects, may not be actionable and/or sufficiently timely for sending an alert to a user regarding for example a hypo or a hyper glucose state since the backfill data is retrospective data, rather than more current, real-time data indicative of a user's current state. But backfill data may provide some insight into past blood glucose states, trends, and can be used to correlate with past activity or food consumption.

The following provides an example use case for backfill data for purposes of illustration. Jane is a Type I diabetic, and an avid surfer. During a surfing session, she has to leave her receiver including a display on land, causing a lost connection between the sensor/transmitter and the receiver. When Jane comes back in range of receiver after an hour or so of surfing, she checks the receiver for a display of her glucose state. Within a few minutes, the receiver may initially present her non-backfill, real-time glucose data, which in this example indicates she has a high glucose state that is just above her hyper alert threshold. As a result, her receiver presents an alert but having missed the previous hour of glucose data, Jane does not have any trend information. Nor does she know if she is at the peak of her glucose level excursion or on the rising or falling edge, so Jane does not know whether she needs to administer insulin. However, within a certain period of time after receiving the real-time sensor date, the receiver may receive backfill data from the sensor transmitter. In this example, the receiver displays the backfill data in a graphically distinct manner (for example, in yellow) from the non-backfill sensor data (which may be displayed in white), so Jane can view a trend graph showing graphically distinct backfill data displayed yellow while more current sensor data is displayed in white. In this way, Jane can see trend data provided by the backfill data, and, more importantly in this example, she can view that the trend indicates that she is past a peak glucose and returning to an acceptable range. The trend may also indicate to Jane how fast her glucose is falling, so she can make a decision that she needs to eat something.

To illustrate further, Jane may be asleep and while sleeping she may miss data capture for a given period of time during the night due to for example Jane covering the sensor transmitter with her body (for example, rolling over on top of the transmitter). In this example, Jane may not want backfill data to be automatically displayed because the automatic insertion of backfill data may mask the nighttime gap(s) in data and mask that the receiver was not receiving data. That is, because the system presented a complete set of data, Jane could have incorrect belief that the system in properly monitoring her through the night and would alarm should a risky situation be presented. To alleviate this potential problem, Jane may want to see the gap(s) or a highlight (or other graphic indication) that graphically indicates that the data is clearly backfill data associated with at least one gap in the transmission of the sensor data. In this way, Jane can readily determine that a problem occurred with the sensor transmitter or receiver during the night. Likewise, Jane may switch receivers using a first receiver during the day and another receiver at night. In this example, highlighting gaps in the sensor data allows Jane to readily determine that the gap was due to the receiver switch.

In some example embodiments, there may be provided ways of handling, at a receiver, backfill data.

In some example embodiments, there may be provided ways of handling backfill data, so that a user may be able to graphically distinguish backfill data from non-backfill data, such as current or real-time data.

In some example embodiments, the receiver may generate a user interface view including a plot, and this plot may be generated to include backfill data and non-backfill data provided by a sensor, such as a CGM sensor.

In some example embodiments, the backfill data may be presented using a graphically distinct indicator, such as a color, a shading, a dashed line, a special icon, and/or the like, to distinguish the backfill data from the non-backfill data.

In some example embodiments, the backfill data may be presented automatically.

In some example embodiments, consent may be provided prior to enabling the presentation of backfill data at a user interface of the receiver.

In some example embodiments, a notification may be generated and presented at a user interface to indicate that the data corresponds to backfill data.

In some example embodiments, a notification may indicate that an event would have been considered an alert, such as a glucose measurement above or below a threshold value, but was not flagged as an alert as the event was found in backfill data, rather than non-backfill data.

In some example embodiments, a receiver may receive backfill data representative of sensor data stored, at a continuous blood glucose sensor and transmitter assembly, due to a loss of a wireless link between the receiver and the continuous blood glucose sensor and transmitter assembly. The receiver may generate at least one of a notification or a graphically distinct indicator for presentation at a display of the receiver, the at least one of the notification or the graphically distinct indicator enabling the backfill data to be graphically distinguished, when presented at the display, from non-backfill data. The receiver may generate a view including the backfill data, the non-backfill data, and the generated at least one of the notification or the graphically distinct indicator.

Before providing additional description regarding backfill handling, the following provides a description of examples of systems in which the data backfill handling disclosed herein may be implemented.

FIG. 1 is a schematic view of a continuous analyte sensor system 100 attached to a host and communicating with a number of example devices 110-113, in accordance with some example embodiments. A transcutaneous analyte sensor system comprising an on-skin sensor assembly 101 is fastened to the skin of a host via a disposable housing (not shown). The system includes a transcutaneous analyte sensor 102 and a transmitter/sensor electronics unit 104 for wirelessly transmitting analyte information to a receiver. In alternative embodiments, the sensor may be non-invasive.

The system 100 may also include at least one remote computer 145A-B that can be accessed by the host-patient or others such as a remote follower (for example, a parent or caregiver authorized to receive alerts and/or sensor data for a certain host patient). The remote computers 145A-B may download from a server a CGM application 135A-B for receiving, transmitting, and/or displaying CGM data as well as other types of data. The remote computers 145A-B may receive the alerts and/or sensor data from a remote server 130 (labeled server), although the alerts and/or sensors may be received from at least one of the devices 110-113 and/or the transmitter 104. In some embodiments, each of the remote computers 145A-B can be a mobile smart device, such as a mobile smart phone or tablet computer.

During use, a sensing portion of the sensor 102 is under the host's skin, and a contact portion of the sensor 102 is electrically connected to the electronics unit 104. The electronics unit 104 engages a housing (not shown), and the sensor extends through the housing. The housing, which maintains the assembly 101 on the skin and provides for electrical connection of the sensor 102 to sensor electronics provided in the electronics unit 104, is attached to an adhesive patch fastened to the skin of the host.

The on-skin sensor assembly 101 may be attached to the host with an applicator (not shown) adapted to provide convenient and secure application. Such an applicator may also be used for attaching the electronics unit 104 to a housing, inserting the sensor 102 through the host's skin, and/or connecting the sensor 102 to the electronics unit 104. Once the electronics unit 104 is engaged with the housing and the sensor 102 has been inserted and is connected to the electronics unit 104, the applicator detaches from the sensor assembly.

The continuous analyte sensor system 100 includes any sensor configuration that provides an output signal indicative of a concentration of an analyte. The output signal, which may be in the form of, for example, sensor data, such as a raw data stream, filtered data, smoothed data, and/or otherwise transformed sensor data, is sent to the receiver, which is described in more detail below. This sensor data may comprise backfill data and/or non-backfill data. The backfill data may represent data that would have been sent by the transmitter 104 to the receiver but for a lack an available link or some other type of error. As such, backfill data represents sensor data that has supposed to be transmitted at a certain time but has not, so the unsent sensor data is stored and then later sent as backfill data. The backfill data may be stale in the sense that it might not capture the current glucose state of the host wearing the sensor. With stale data, a user may not want to take action based on the sensor data, while with more current non-backfill data, a user may take action based on the sensor data. The non-backfill data may represent real-time data sent from the transmitter to the receiver. For example, a sensor transmitter 104 may have one or more scheduled transmissions during which sensor data is sent to a receiver, such as device 112. If the scheduled data transmission is missed for whatever reason, the data may be considered stale and thus be treated as backfill data when subsequently sent to the receiver.

In various embodiments, the analyte sensor system 100 includes a transcutaneous glucose sensor, a subcutaneous glucose sensor, a continuous refillable subcutaneous glucose sensor, or a continuous intravascular glucose sensor, for example. In some embodiments, the sensor 102 extends through a housing (not shown), which maintains the sensor on the skin and provides for electrical connection of the sensor-to-sensor electronics, provided in the electronics unit 104. In some embodiments, the sensor 102 is formed from a wire. For example, the sensor can include an elongated conductive body, such as a bare elongated conductive core (e.g., a metal wire) or an elongated conductive core coated with one, two, three, four, five, or more layers of material, each of which may or may not be conductive. The elongated sensor may be long and thin, yet flexible and strong. For example, in some embodiments the smallest dimension of the elongated conductive body is less than about 0.1 inches, 0.075 inches, 0.05 inches, 0.025 inches, 0.01 inches, 0.004 inches, or 0.002 inches. Preferably, a membrane system is deposited over at least a portion of electroactive surfaces of the sensor 102 (including a working electrode and optionally a reference electrode) and provides protection of the exposed electrode surface from the biological environment, diffusion resistance (limitation) of the analyte if needed, a catalyst for enabling an enzymatic reaction, limitation or blocking of interferents, and/or hydrophilicity at the electrochemically reactive surfaces of the sensor interface.

The membrane system may include a plurality of domains, for example, an electrode domain, an interference domain, an enzyme domain (for example, including glucose oxidase), and a resistance domain, and can include a high oxygen solubility domain, and/or a bioprotective domain. The membrane system may be deposited on the exposed electroactive surfaces using known thin film techniques (for example, spraying, electro-depositing, dipping, etc.). In some embodiments, one or more domains are deposited by dipping the sensor into a solution and drawing out the sensor at a speed that provides the appropriate domain thickness. However, the membrane system can be disposed over (or deposited on) the electroactive surfaces using any known method.

In the illustrated embodiment, the electronics unit 104 is releasably attachable to the sensor 102, which together form the on-skin sensor assembly 101. The electronics unit 104 includes electronic circuitry associated with measuring and processing the continuous analyte sensor data, and is configured to perform algorithms associated with processing and calibration of the sensor data. The electronics unit 104 may include hardware, firmware, and/or software that enable measurement of levels of the analyte via a glucose sensor, such as the analyte sensor 102. For example, the electronics unit 104 can include a potentiostat, a power source for providing power to the sensor 102, other components useful for signal processing and data storage, and preferably a telemetry module for one- or two-way data communication between the electronics unit 104 and one or more receivers, repeaters, and/or display devices, such as the devices 110-113 (which may also be referred herein as user equipment). Sensor electronics within the electronics unit 104 can be affixed to a printed circuit board (PCB), etc., and can take a variety of forms. For example, the electronics can take the form of an integrated circuit (IC), such as an application-specific integrated circuit (ASIC), a microcontroller, and/or a processor. The electronics unit 104 may include sensor electronics that are configured to process sensor information, such as storing data, analyzing data streams, calibrating analyte sensor data, estimating analyte values, such as estimated glucose values (EGVs), comparing estimated analyte values with time corresponding measured analyte values, analyzing a variation of estimated analyte values, and/or the like.

One or more repeaters, receivers and/or display devices may be operatively linked to the electronics unit 104. The repeaters, receivers, and/or display devices (also referred to herein more generally as "receivers" 110-113) receive data from the electronics unit 104, which is also referred to as the transmitter 104 and/or sensor 102 electronics herein. In some embodiments, the repeaters, receivers, and/or display devices can also transmit data to the electronics unit 104, such as one or more reference values used by the sensor electronics unit 104 to calibrate sensor data. The sensor data can be transmitted from the sensor electronics unit 104 to one or more of the key fob repeater 110, the medical device receiver 111, the smartphone 112, the portable or tablet computer 113, and/or the like. Also, in some embodiments the repeaters, receivers, and/or display devices may transmit data, such as data received from the sensor electronics unit 104, to one another through a wireless connection or a wired connection.

In addition, the repeaters, receivers, and/or display devices may transmit data to one another or to remote server 130 through a wireless connection and/or a wired connection via network 120. The remote server 130 may have at least one processor and at least one memory storage device, such as a database, that stores and processes data received from one or more of the key fob repeater 110, the medical device receiver 111, the smartphone 112, the portable or tablet computer 113. In some example embodiments, a remote device, such as remote computers 145A-B, may couple to the remote server 130 to access sensor data associated with a given host couple to the sensor/transmitter. For example, a remote follower, such as a caregiver, a parent, and/or the like, may receive sensor data and associated alerts to remotely follow a host-user at receiver 112.

In some embodiments, analyte values are displayed on a display device 110-113. In some embodiments, prompts or messages can be displayed on the display device to convey information to the user, such as reference outlier values, requests for reference analyte values, therapy recommendations, deviation of the measured analyte values from the estimated analyte values, etc. The displayed analyte values may include the most recently measured or real-time analyte data values as well as past analyte values. Additionally, prompts can be displayed to guide the user through calibration or troubleshooting of the calibration.

Data output from the on-skin sensor assembly 101 can be provided via wired and/or wireless, one- or two-way communication between the receiver 110-113 and an external device. The external device can be any device that interfaces or communicates with the receiver. In some embodiments, the external device is a computer, and the receiver is able to download current and/or historical data for retrospective analysis by a physician, for example. In some embodiments, the external device is a modem, and the receiver is able to send alerts, warnings, emergency messages, etc., via telecommunication lines to another party, such as a doctor and/or a family member, at a remote computer 145A-B. In some embodiments, the external device is an insulin pen or insulin pump, and the receiver is able to communicate therapy recommendations, such as an insulin amount and a time to the insulin pen or insulin pump. The external device can include other technology or medical devices, for example pacemakers, implanted analyte sensor patches, other infusion devices, telemetry devices, etc. The receiver may communicate with the external device, and/or any number of additional external devices, via any suitable communication protocol, including radio frequency (RF), Bluetooth, universal serial bus (USB), any of the wireless local area network (WLAN) communication standards, including the IEEE 802.11, 802.15, 802.20, 802.22 and other 802 communication protocols, ZigBee, wireless (e.g., cellular) telecommunication, paging network communication, magnetic induction, satellite data communication, GPRS, 3G, 4G, 5G, LTE, ANT, and/or a proprietary communication protocol.

Figure 2:
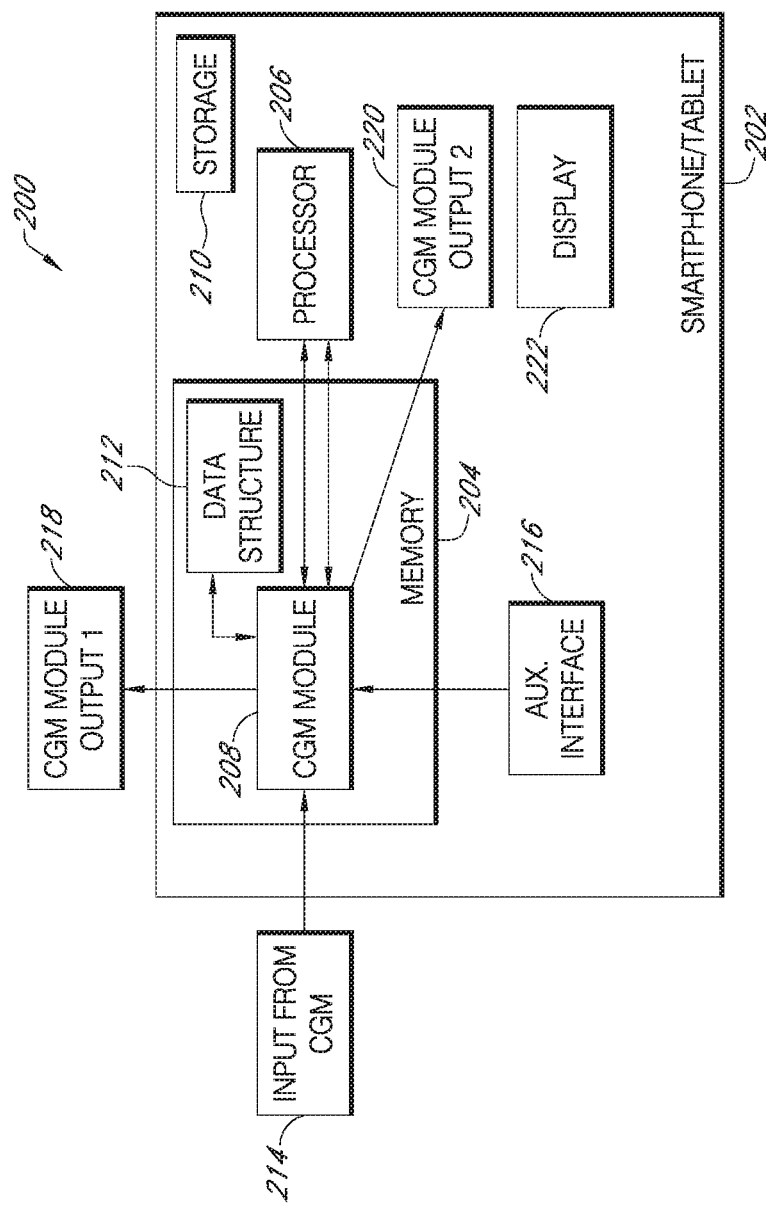
FIG. 2 illustrates a functional block diagram of a mobile device used with the continuous analyte sensor system, in accordance with some example embodiments.

FIG. 2 is a functional block diagram of an embodiment of a system 200 for leveraging mobile device features in continuous glucose monitoring, according to some example embodiments. The system 200 may include a mobile device 202, which may be any type of computing device, such as display devices 110-113, capable of receiving one or more inputs and producing an output. Examples of the mobile device include a smartphone, a tablet computing device, a laptop, and/or the like.

The mobile device 202 may include a memory 204 and a processor 206. The memory 204 may provide the processor 206 access to data and program information that is stored in the memory 204 at execution time. Typically, the memory 204 may include random access memory (RAM) circuits, read-only memory (ROM), flash memory, etc., or a combination of such devices. The processor 206 may be, or may include, one or more programmable general-purpose or special-purpose microprocessors 206, digital signal processors 206 (DSPs), programmable controllers, application specific integrated circuits (ASICs), programmable logic devices (PLDs), etc., or a combination of such hardware-based devices.

In accordance with some embodiments, the processor 206 may execute a continuous glucose monitoring (CGM) application 208 (labeled CGM module) out of the memory 204. As used herein, the term continuous glucose monitoring module or CGM application should be construed broadly to include not just the application itself, but also the CGM application may be able to include other CGM-related functions including integration with other diabetes management devices, including insulin delivery therapies such as insulin pumps, insulin pens, or other drugs useful for the treatment of diabetes. In other words, the CGM application may perform other functions besides monitoring blood glucose. It could, for example, determine that a user's blood glucose level is high, and then transmit a signal to the user's insulin pump to administer a quantity of insulin to bring the user's blood glucose level down.

A software and/or firmware component of the CGM application 208 may be stored in storage 210 available to the mobile device 202, and loaded into the memory 204 at execution time. The storage 210 may be any non-transitory computer readable media including, but not limited to, a hard disk, EEPROM (electrically erasable programmable read only memory), a memory stick, or any other storage device type. The memory 204 may contain one or more data structures 212 that the CGM application 208 accesses during execution. For example, the CGM application 208 may receive an input and store the input as an input parameter in a data structure 212 in the memory 204 for later processing.

In certain embodiments, the CGM application 208 may be embodied as downloadable software that a user may download from a server, such as remote server 130, and/or a website through a wired or wireless connection. For example, the user may access the server using an application already installed on the user's mobile device. The user may then download and install the CGM application 208 with the aid of the application. The user may then configure the CGM application 208. For example, the configuration may include setting the user's personal preferences and/or settings, such as contacts, events, modes, profiles, and/or the like. The configuration may be done manually, such as by selecting various options from menus, or automatically. In automatic configuration, the CGM application 208 reads the user's preferences and/or settings that are stored on the mobile device. The CGM application 208 would first discover what other applications are installed on the mobile device, and then access those applications' data stored in the mobile device's storage and/or remote storage accessible by the mobile device 202 to initially populate the CGM application 208 during set up. For example, the CGM application 208 may be downloaded from a server at a website such as an application store, and downloaded into a mobile device.

Figure 3:
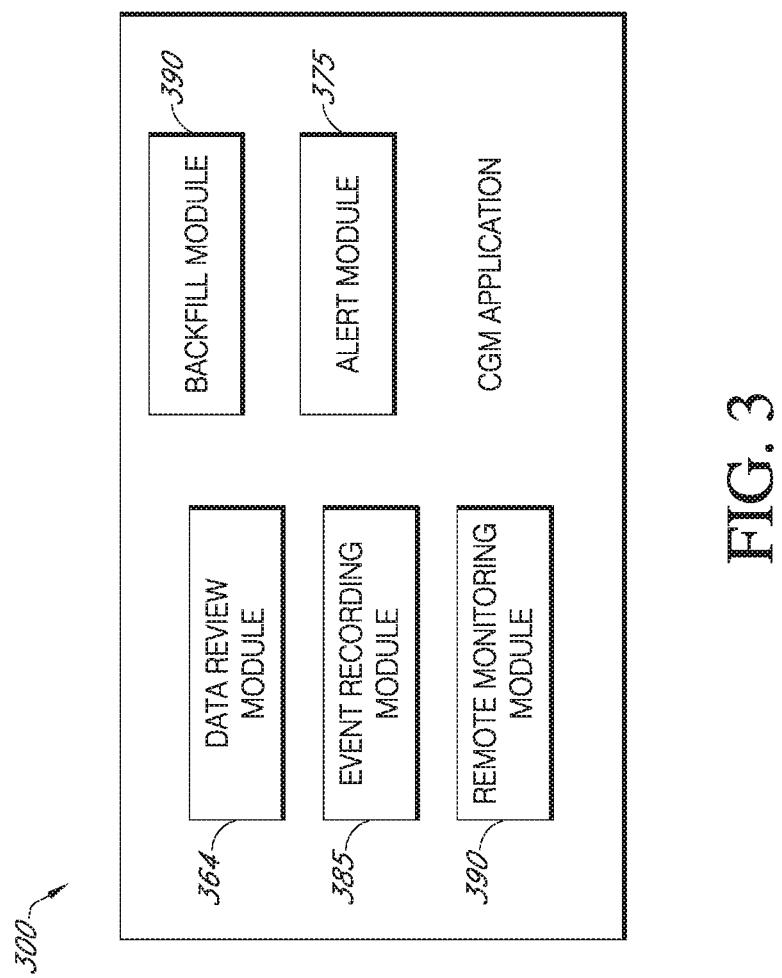
FIG. 3 illustrates a functional block diagram of the CGM application, in accordance with some example embodiments.

FIG. 3 illustrates a functional block diagram of the CGM application 208 running on mobile device 202, in accordance with some example embodiments. This block diagram includes various software modules (for example, functions or features) that control the behavior of CGM application 208. The software modules of CGM application 208 may include a data review module 364, an event recording module 385, a remote monitoring module 290, an alert module 375, and a backfill module 390. Each of these modules is further described below.

Data review module 364 may display a patient's glucose levels. The data review module 364 may provide information regarding a patient's current glucose level and its rate of change. Data review module 364 may also display a trend graph that illustrates variations in a patient's glucose level over time and may indicate the presence of a clinical risk to the patient.

Remote monitoring module 290 may share a patient's glucose level information with other users, such as one or more remote monitors or followers. As described above with respect to system 200, a remote server 130 may provide this information to secondary computing devices such as remote computers 145A and/or 145B. A patient may use remote monitoring module 290 to invite remote monitors or followers to receive this information and customize the type of information that may be viewed by invited remote monitors or followers. It is contemplated that, in some example embodiments, a patient may upload backfill data (e.g., to the remote server 130) that is received from the transmitter 104. The uploaded backfill data may then be shared with a follower via a remote computer and/or a display device. This may allow the follower to be in synchronization with the glucose level information of the patient.

A patient may use event recording module 385 to enter and review events. Events may include food intake, medication intake, exercise, and the like. By recording this information, the patient may obtain a better understanding of how different types of events may influence his or her glucose levels.

Alert module 375 may generate various alarms or alerts. For example, alert module 375 may be configured to generate an alarm if a patient's glucose level drops below or rises above a predetermined threshold value. A patient may use alert module 375 to set alerts for different parameters and designate which alerts to propagate to the remote monitors.

Backfill module 390 may handle backfill data including control of when backfill data is provided to the receiver, how the backfill data is presented, whether to display backfill data, whether to display backfill data in a graphically distinct way from non-backfill data, whether to trigger an alert based on backfilled data, and/or other aspects described herein associated with the backfill data. Examples of operations under the control of the backfill module 390 are further described below with respect to FIGS. 4-11. It is contemplated that some example embodiments described herein may be implemented using distributed system architecture.

Figure 4:
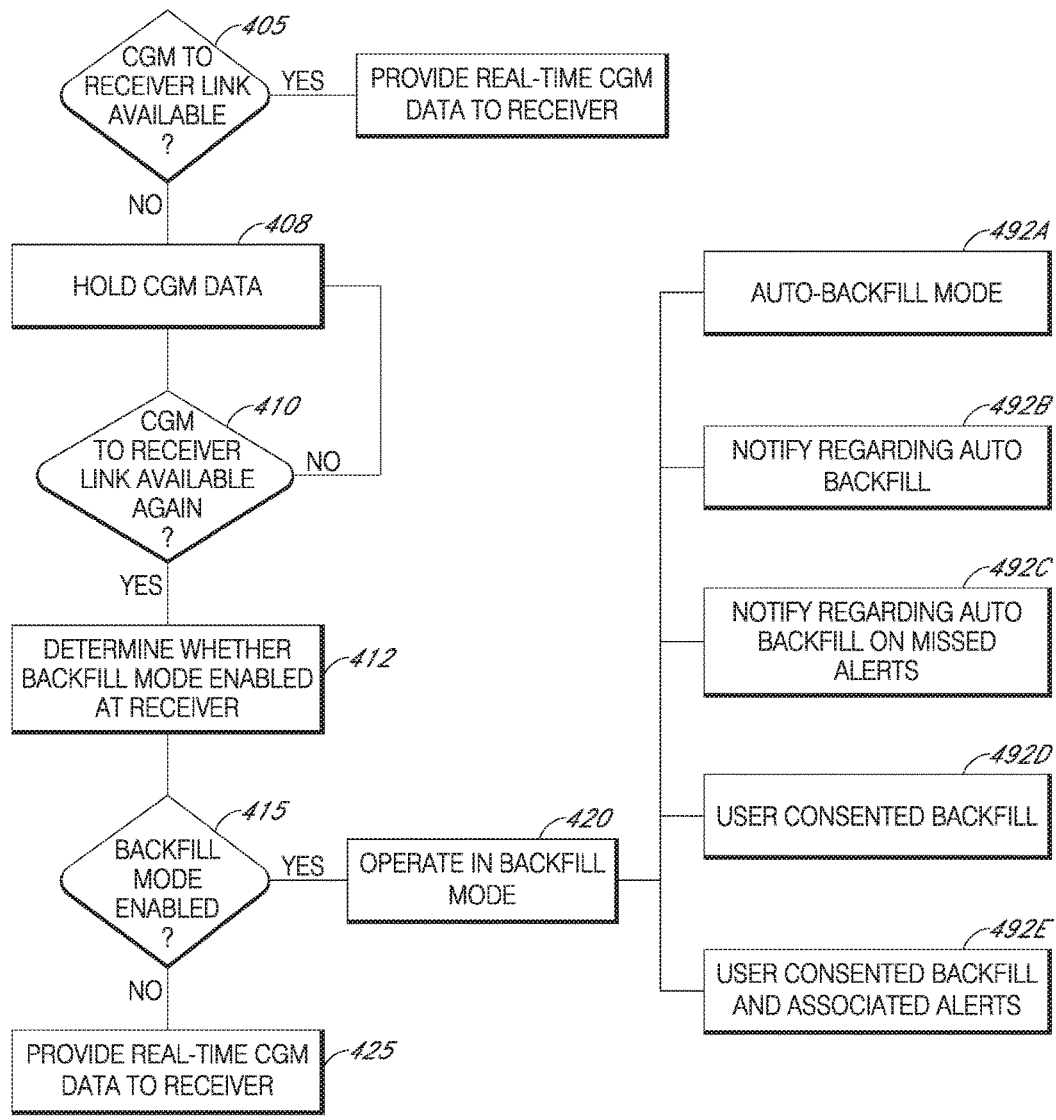
FIG. 4 depicts an example process 400 for handling backfill data, in accordance with some example embodiments.

FIG. 4 depicts an example of a process 400 for handling backfill data, in accordance with some example embodiments. The description of FIG. 4 also refers to FIGS. 1-3.

The link between the transmitter 104 and the receiver, such as smartphone 112, may be available (yes at 405). When this is the case, the transmitter 104 may, at 407, transmit to the receiver 112 sensor data, such as estimated glucose values (EGV), CGM sensor data, and/or the like, via the available wireless link between the transmitter and receiver. This transmission may comprise a scheduled transmission. For example, the link between the transmitter 104 and the receiver 112 may be established and thus available from time to time when requested by the transmitter or receiver and/or in accordance with a schedule (for example, every 10 minutes, every 5 minutes, every 4 minutes, and so forth although other times may be used as well as times that are not periodic).

However, when the wireless link is not available (no at 405), the transmitter 104 may hold, at 408, the sensor data by storing the sensor data in memory, for example. The link may not be available for a variety of reasons. For example, the distance between the transmitter 104 and the receiver 112 may be too large and beyond the RF range of the transmitter. Alternatively or additionally, a device, such as the receiver, may be powered off. Alternatively or additionally, a host patient may roll over on top of the transmitter 104 and attenuate the link between the transmitter and receiver in such a way that the link cannot establish a link to carry the sensor data. In these examples, the receiver may not be able to receive the sensor data. In some instances, the link may be established and thus available at 405 but CGM data is not available for transmission due an error, malfunction, or other reason. When this is the case, the transmitter may hold, at 408, the sensor data by storing the sensor data in memory as well, even though the link is available.

While the link between the transmitter and receiver is not available, transmitter 104 may continue to hold the sensor data (no at 410). Although the previous example describes the sensor being held due to an unavailable link, sensor data may be held for other reasons as noted.

When the link becomes available again (and/or there is no error or malfunction preventing the transmitter from sending sensor data to the receiver), the transmitter 104 may reinitiate transmission of sensor data to the receiver 112. To that end, a determination may be made by at least one of the sensor 102/transmitter 104 and/or the receiver 112 regarding whether a backfill mode is enabled (yes at 410, and 412). For example, if backfill mode is not enabled, the sensor 102/transmitter 104 may proceed to send non-backfill, current/real-time sensor data, at 425, to the receiver but the backfill data (which missed its original transmission window and was accumulated when the link was not available) may not be sent by the sensor 102/transmitter 104 to the receiver 112 (or if sent, disregarded by the receiver or sent at a later time or when requested). Whether backfill mode is enabled at the receiver may be implemented at the receiver in a variety of ways. For example, a user may configure the receiver to allow backfill data to be sent and/or displayed at the receiver as backfill data. The user may also configure the receiver to display at the receiver the backfill way in a graphically distinct way from non-backfill data. The user may be any type of user including the host patient, a caregiver, a default factory setting of the receiver, and/or the like.

In some example embodiments, backfill data may always be sent to the receiver 112. However, a user may be given the option to enable whether or not to display the backfill data. For example, the user may configure whether the backfill data should be presented at receiver 112, and the user may also configure whether or not the backfill data is presented at receiver 112 in a graphically distinct way from non-backfill data. The user may also be allowed to configure whether backfill data is transmitted to the receiver 112. In some example embodiments, certain modes of the receiver 112 may be configured to always backfill data for presentation at the receiver. For example, in an artificial pancreas setting (e.g. CGM data automatically controlling medication administration), the receiver may be configured to always backfill data. Moreover, the order of data transmission may also be configured. For example, the receiver, when in a certain mode, may be configured to request sensor data transmission in chronological order. Alternatively or additionally, the receiver, when in a certain mode, may be configured to request sensor data transmission in reverse chronological order. Alternatively or additionally, the receiver, when in a certain mode, may be configured to request non-backfill data transmission before backfill data transmission. Alternatively or additionally, the receiver, when in a certain mode, may be configured to request backfill data transmission before non-backfill data transmission.

In some example embodiments, more recent backfill data may be transmitted more frequently when compared older, backfill data. For example, more recent backfill data may be transmitted at twice the rate of older backfill data. To illustrate further, given six transmission windows or time periods, the more recent backfill data may be sent in the first two windows, followed by the older backfill data in the next window, followed by more recent backfill data in the next two windows, followed by older backfill data in the next window, and so forth, although other rates may be configured as well. In some example embodiments, a threshold may be defined to determine whether data is treated as older backfill data. Moreover, the rate for the new backfill data may be configured and/or predetermined, in some example embodiments. Likewise, the rate for the older backfill data may be configured and/or predetermined, in some example embodiments. By sending more recent backfill data, more accurate processing of alarms, alerts, and/or the like may be realized.

Furthermore, non-backfill data may be transmitted more frequently when compared backfill data. For example, non-backfill data may be transmitted at twice the rate of older backfill data, although other rates may be used as well. In some example embodiments, the rate for the non-backfill data and the rate of the backfill data may be configured and/or predetermined and/or configurable by a user.

In some example embodiments, the system may be configured to operate, at 420, in a backfill mode. Moreover, the backfill mode may include one or more configurations as further described herein with respect to 492A-E for example. In some example embodiments, the backfill mode is controlled by the backfill module 390. The control may be user configurable or automatically controlled, and this control may include enabling backfill, configuring the backfill mode, generating views and notifications regarding backfill, generating views requesting consent to backfill, and/or the like.

In some example embodiments, the system 100 (or portions therein) may automatically enter into a backfill configuration mode at 492A. During this backfill configuration mode, transmitter 204 may initially send to the receiver, such as smartphone 112/202 for example, non-backfill data, such as current or real-time CGM sensor data that can be actionable with respect to alerts and the like. Data that is sent when scheduled, as noted above, may be considered current or real-time. Because the backfill data may be considered retrospective and likely not actionable with respect to alerts, transmitter 104 may, in some example embodiments, send the backfill data after at least a portion of the real-time data is sent to the receiver. In the auto backfill configuration mode 492A, the backfill data may thus be sent automatically, without requiring consent and/or action by the user at the receiver.

Although the previous example refers to backfill data as not being actionable, backfill data may be actionable in some instances. For example, the backfill data may be stale but it may be related to more recently received sensor data that indicates the need for an action, such as an alert (for example, glucose trending lower or higher). Furthermore, although the previous example describes the backfill data being sent after the real-time data is sent to the receiver, the backfill data may be sent at other times as well.

At 492A, the receiver 112 may automatically receive backfill data and generate a view including a plot of sensor data, such as CGM sensor data, for display at the receiver's user interface. This view may depict the backfill data in a graphically distinct way from non-backfill data. In some example embodiments, backfill data may be depicted in a different color, when compared to non-backfill CGM data. Alternatively or additionally, backfill data may be depicted as dotted lines or symbols, while real-time CGM data may be depicted as solid lines or symbols. Alternatively or additionally, backfill data may be depicted as solid lines or symbols, while real-time (for example, non-backfill) CGM data may be depicted as dotted lines or symbols. Alternatively or additionally, backfill data may have a transparent overlay placed above (or below) the backfill data to graphically distinguish it from real-time CGM data (which in this example may not include a transparent overlay). Although certain examples of graphically distinct indicators are described, other graphically distinct indicators may be used to distinguish backfill data from non-backfill, real-time data. The indicator may correspond to a certain type of indication or how the data is presented.

Figure 5A:
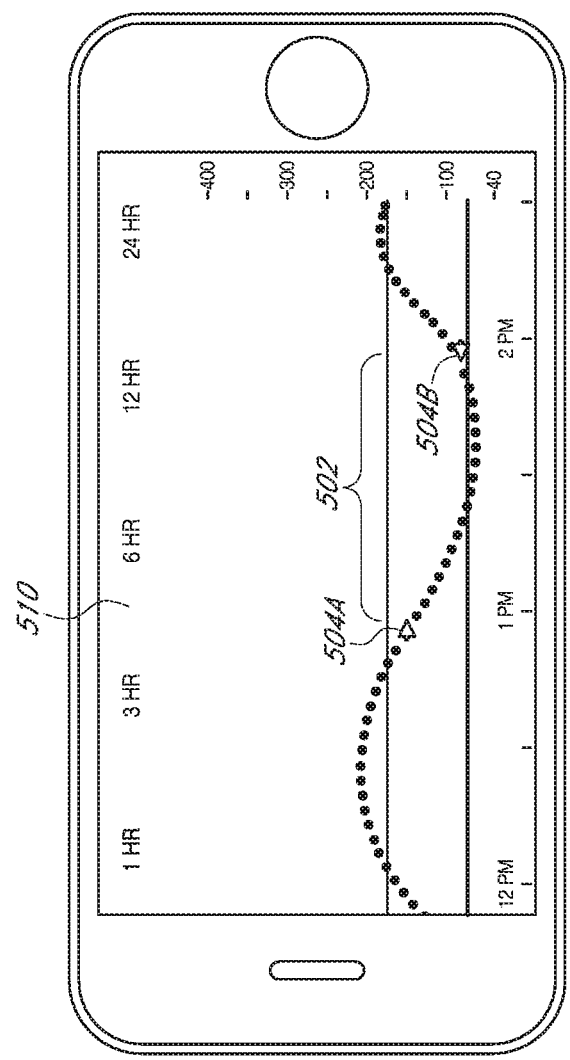
FIGS. 5A-5E depict examples of views associated with backfill data handling, in accordance with some example embodiments.

FIG. 5A depicts an example of a user interface view 510 of a plot presented at a receiver of CGM sensor data (which may be provided by for example sensor 102 and transmitter 104). In the example of FIG. 5A, backfill data is depicted within bracket 502, while non-backfill CGM values are located outside of bracket 502. In the example of FIG. 5A, the backfill data is presented in a graphically distinct way from the non-backfill data, such as more current or real-time CGM sensor data sent when the link is available (for example, established) between the transmitter and receiver. When the receiver receives the backfill data, the receiver generates a view including graphically distinct icons 504A-B. As shown, the graphically distinct icon 504A includes an arrow pointing towards the right of the display, while graphically distinct icon 504B includes an arrow pointing towards the left of the display. In this way, a user looking at view 510 including graphically distinct icons 504A-B would recognize that the data points between the arrows of the graphically distinct icons 504A-B are backfill data, while the values outside of the graphically distinct icons 504A-B are non-backfill data, such as the real-time CGM data.

Figure 5B:
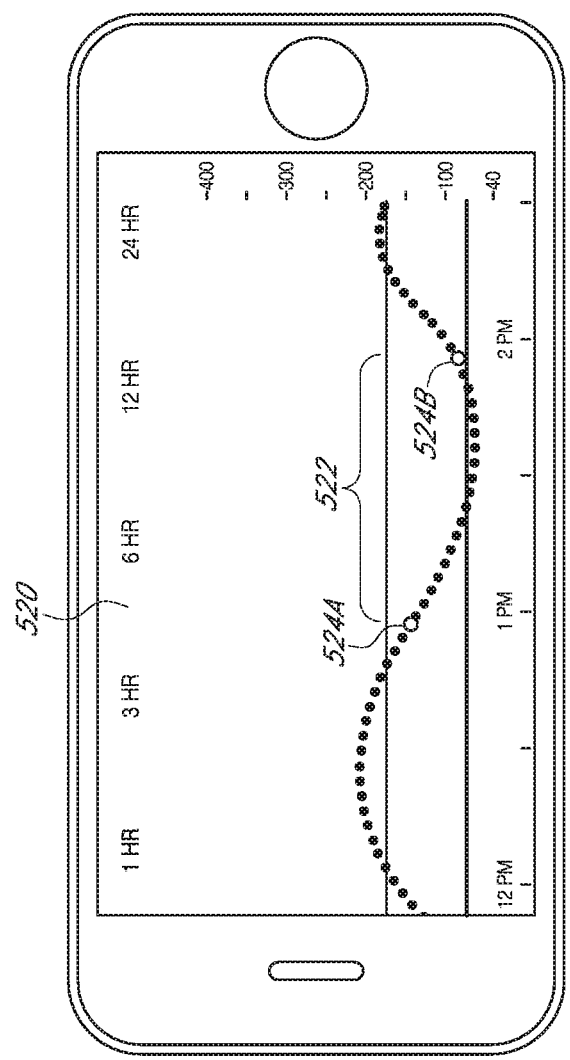

FIG. 5B depicts another example of a user interface view 520 of a plot presented at a receiver of CGM sensor data that is sent by for example a CGM sensor 102 and transmitter 104. In the example of FIG. 5B, backfill data is depicted within bracket 522, so the data points between 524A and 524B correspond to backfill data, while other CGM values outside 522 represent non-backfill data, such as the more current or real-time CGM data. The hollow, circular icons 524A-B are graphically distinct to enable distinguishing from non-backfill data outside of 522 (which in this example, includes solid, circular icons). Although the example of FIG. 5B depicts a solid circular icon, the circles can be presented in other graphically distinct ways (for example, a certain color, shape, etc.) to indicate the start of a sequence of backfill data and another graphically distinct circular icon may be used to indicate the end of a sequence of backfill data. A user looking at view 520 including graphically distinct icons 524A-B would graphically recognize that the data points between graphically distinct icons 524A-B are backfill data while the values outside of the graphically distinct icons 524A-B are non-backfill data. In this way, a viewer of the view 520 can assess past trends in backfill, alerts (which may have occurred in the past but may no longer be relevant), and/or make other diagnostic decisions.

Figure 5C:
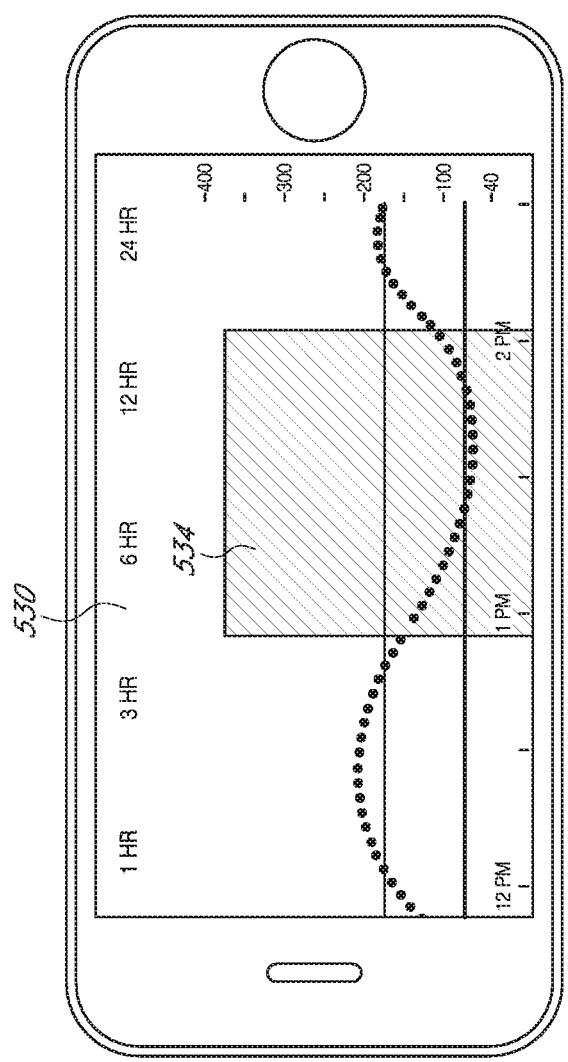

FIG. 5C depicts another example of a user interface view 530 of a plot presented at a receiver of CGM sensor data sent by for example a CGM sensor 102 and transmitter 104. In the example of FIG. 5C, an overlay, such as graphically transparent overlay 534, is placed on the backfill data to indicate that the data under the overlay is backfill data, while data values outside 534 represent non-backfill data. A user looking at view 530 would graphically recognize that the CGM data values under overlay 534 are backfill data while the values not covered by the overlay are non-backfill data. Although the previous example describes the overlay over the non-backfill data, the overlay may be placed over the real-time, non-backfill data instead to distinguish the backfill data from the backfill data.

Figure 5D:
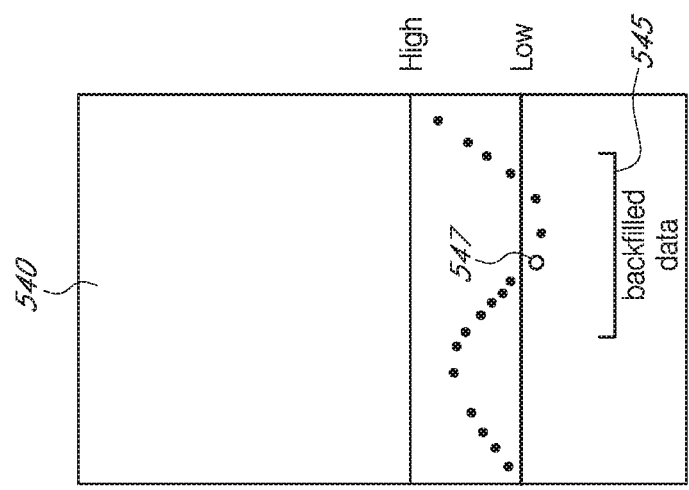

FIG. 5D depicts another example of a view 540 of a plot presented at a receiver of CGM data sent by for example a CGM sensor 102 and transmitter 104. In the example of FIG. 5D, a graphically distinct indicator 545 indicates backfill data. In this example, the alert 547 that would have been triggered (but for the backfill and non-available link) is also indicated with a graphically distinct indication 547, which in this example is a larger symbol, when compared to symbols. The missed alert may be communicated in other ways as well. For example, a notification maybe presented at the receiver's user interface to indicate that during the time the link was unavailable an alert occurred at a certain time as determined from the backfill data. Referring again to FIG. 5D at 545, the data was below a low threshold and came back above the low threshold. Because the receiver 112 was not receiving sensor data during the time period associated with the backfill data at 545, an alert would not have been triggered during that time period. However, the alert may, in some example embodiments, may be triggered after the backfill data is received.

Figure 5E:
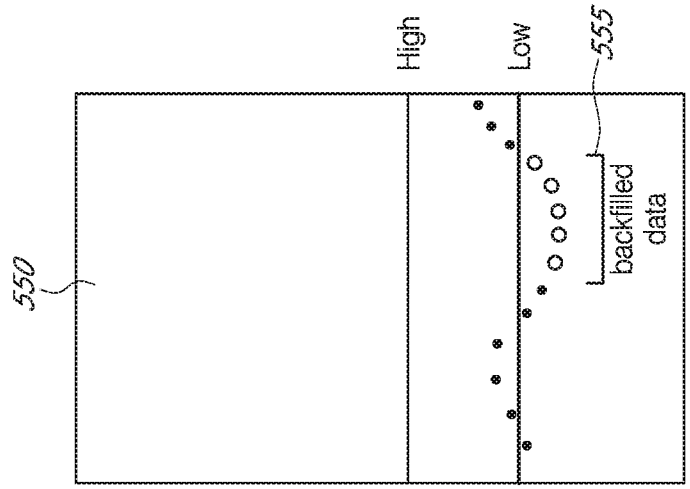

FIG. 5E depicts another example of a view 550 of a plot presented at a receiver of CGM data that is sent by for example sensor 102 and transmitter 104. In the example of FIG. 5E, backfill data is indicated by symbols that are hollow as shown at 555, when compared to non-backfill data that, in this example, are shown as solid circles or symbols, although other graphically distinct colors, shading, blinking dots, etc. may be used as well.

Referring again to FIG. 4, the backfill mode may be configured in a notify regarding auto backfill mode 492B. When this is the case, the receiver may generate a notification for presentation at the receiver's user interface, and this notification may indicate that backfill data is being presented automatically.

Figure 6:
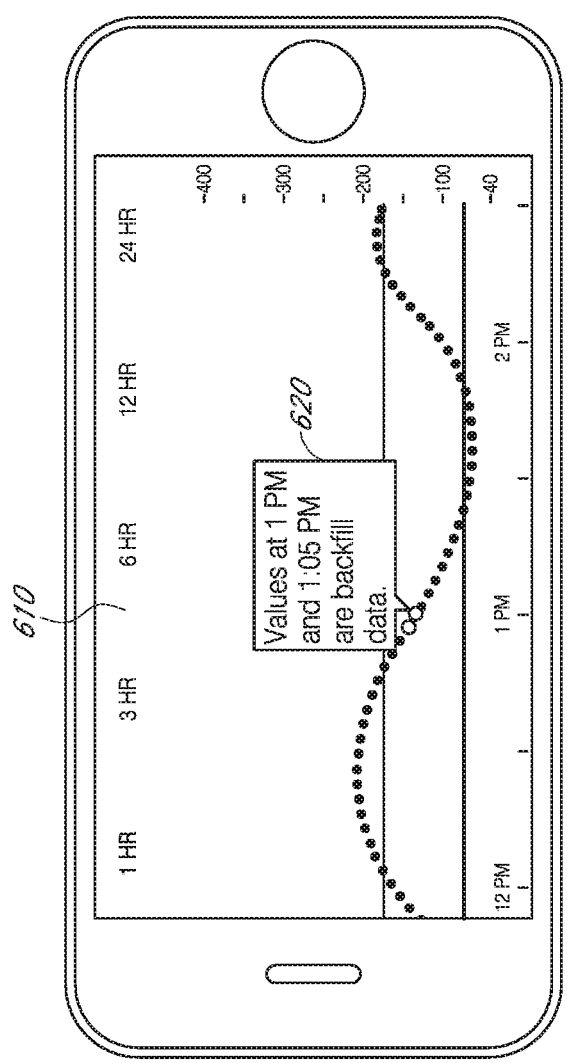
FIG. 6 depicts an example of a notification window indicating that a plotted value is backfill data, in accordance with some example embodiments.

FIG. 6 depicts an example of a notification generated while in notify regarding auto backfill mode 492B. The notification may be permanent or temporary. For example, the notification may disappear (for example, not visible on the display) after the user acknowledges the notification. Alternatively or additionally, the notification may disappear after a predetermined amount of time. Alternatively or additionally, the notification may only appear when the number of backfilled data points exceeds a threshold.

The receiver, such as receiver 112, may generate view 610 depicting a notification 620 generated for presentation at a user interface of the receiver. In this example, the notification indicates that two of the values are backfill data, although the notification may indicate other quantities of backfill data as well. The notification may include the times of the values. Moreover, the notification may also include whether the CGM backfill values would have triggered an alert condition, such as glucose above or below a given blood glucose value threshold. Alternatively or additionally, if more than a plurality of data points are backfilled, the notification may inform the user about a backfill time window and provide a summary of the blood glucose level over that window. For example, the summary may include one or more of EGV in range, number of hypo alerts (which may indicate above a glucose threshold value) missed, percentage of values in range, percentage of value in hypo (for example, below a glucose threshold value), and percentage of values in hyper).

In some example embodiments, the backfill mode may also include providing a notification for presentation at a user interface of the receiver. The notification may indicate that some of the data being presented is backfill data and that an alert was missed during the time associated with backfill data.

Figure 7:
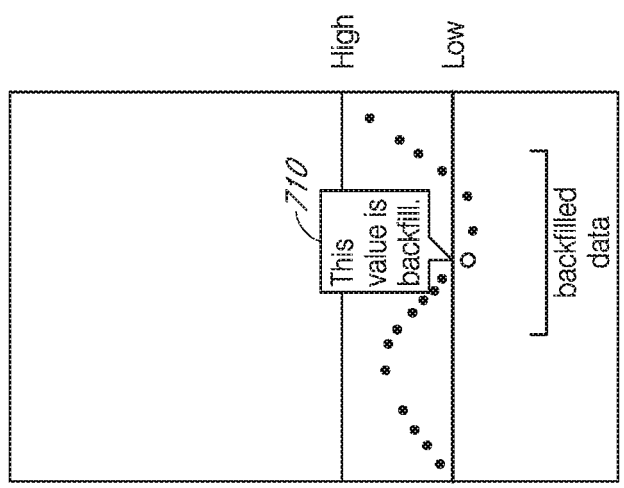
FIG. 7 depicts another example of a notification window, in accordance with some example embodiments.

FIG. 7 depicts an example of a notification 710 for presentation at the receiver's user interface. The notification 710 indicates that an alert was missed due to not having the sensor data to transmit at that point in time. For example, if the user was out-of-range and thus backfill data is stored, when the backfill is later sent to the receiver, the notification 710 may indicate that an alert would have occurred but for the lack of a link and associated backfill data. Moreover, a different graphical indicator, for example the larger circle, may also be used to signal that an alert was missed.

Figure 8:
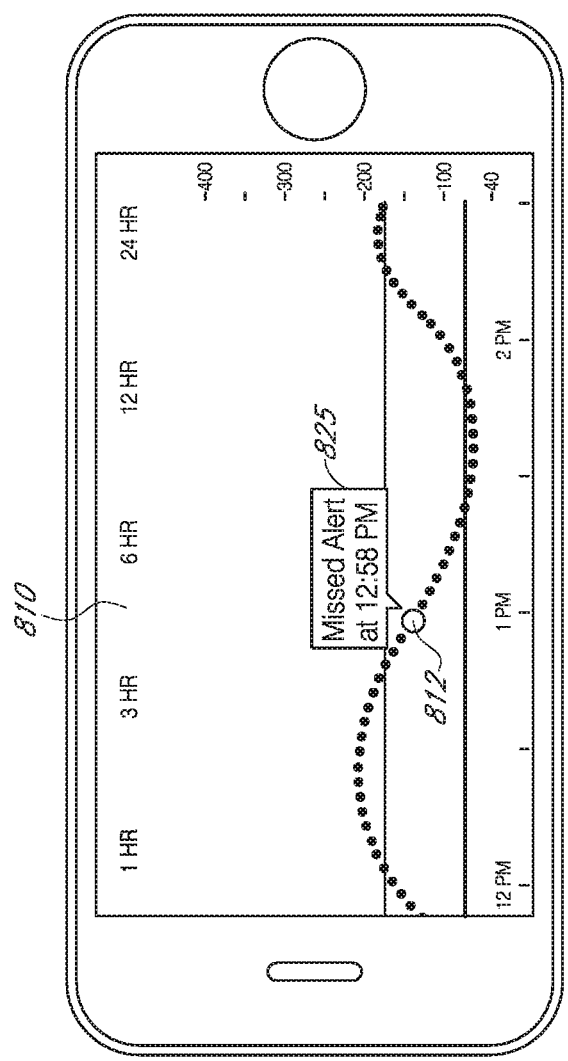
FIG. 8 depicts another example of a notification window indicating a missed alert occurring during a time associated with backfill data, in accordance with some example embodiments.

Referring again to FIG. 4, the backfill mode may be configured in a notify regarding auto backfill on missed alerts 492C. When this is the case, the receiver may automatically include backfill in any views generated associated with missed alerts. Referring to FIG. 8, the receiver may, after receiving the backfill data when the link is again available, generate view 810 including notification 825. In this example, the view includes a graphically distinct indicator 812 to distinguish the backfill data. The view also includes a notification to indicate that there would have been an alert at 1258 PM but it was missed.

In some example embodiments, alerts occurring during a time associated with backfill (for example, a backfill time window during which the transmitter-to-receiver link was unavailable) may be re-evaluated to determine whether to alert the user. In some instances, the alert may not be presented, while in others the alert would be presented.

Figure 9:
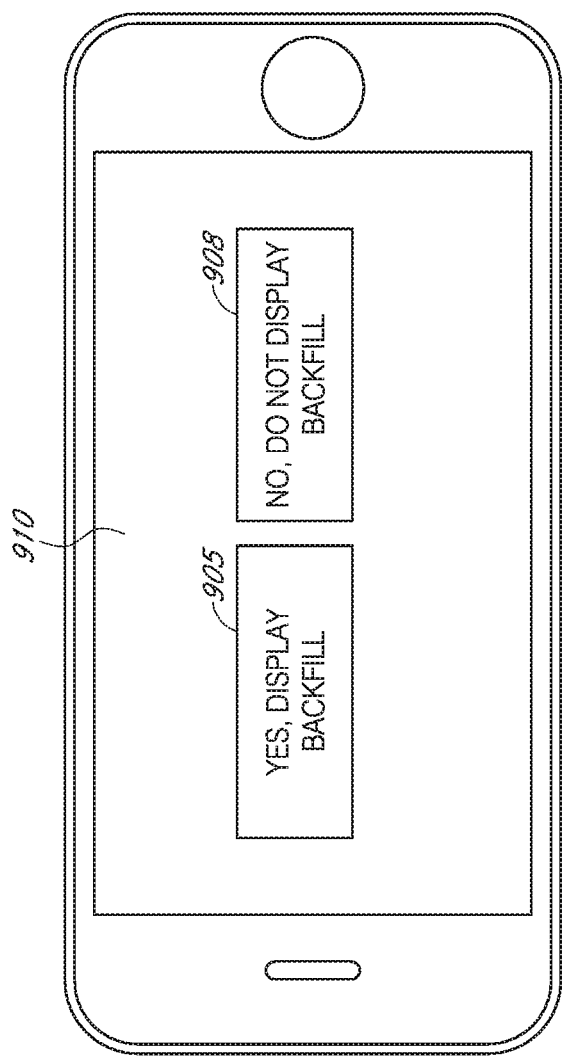
FIG. 9 depicts an example view requesting consent to present backfill data, in accordance with some example embodiments.

Referring again to FIG. 4, the backfill mode may be configured to generate a notification for a request to consent to backfill. For example, the consent may provide consent to receive backfill data and/or consent to present the backfill data on the display. The consent may also include whether or not the displayed backfill data should be indicated graphically distinctly as backfill data. In this user consented backfill mode 492D, receiver may, when consented is granted, automatically include backfill in any views generated. Referring to FIG. 9, the receiver may generate view 910 requesting permission to include backfill data in the displays (yes, 905) or not include backfill data in the displays (no, 908). Moreover, the receiver may generate view 910 after a loss of the available link to query the user regarding interest in seeing the available backfilled data within for example a prior data backfilling time window. If yes 905 is selected, backfill data may be presented and an alert or soft alert may be generated as well. If no is selected 908, the backfill data may not be displayed (although the backfill data may be deleted or stored for display later if requested). Moreover, the selections at 905 and 908 may also include whether missed alerts associated with backfill data should be presented as a notification as shown for example at 825 (FIG. 8).

Although FIG. 9 depicts a notification window to obtain consent, the consent and indication regarding missed alerts may be configured in other ways as well including via a menu or drop down.

Figure 10:
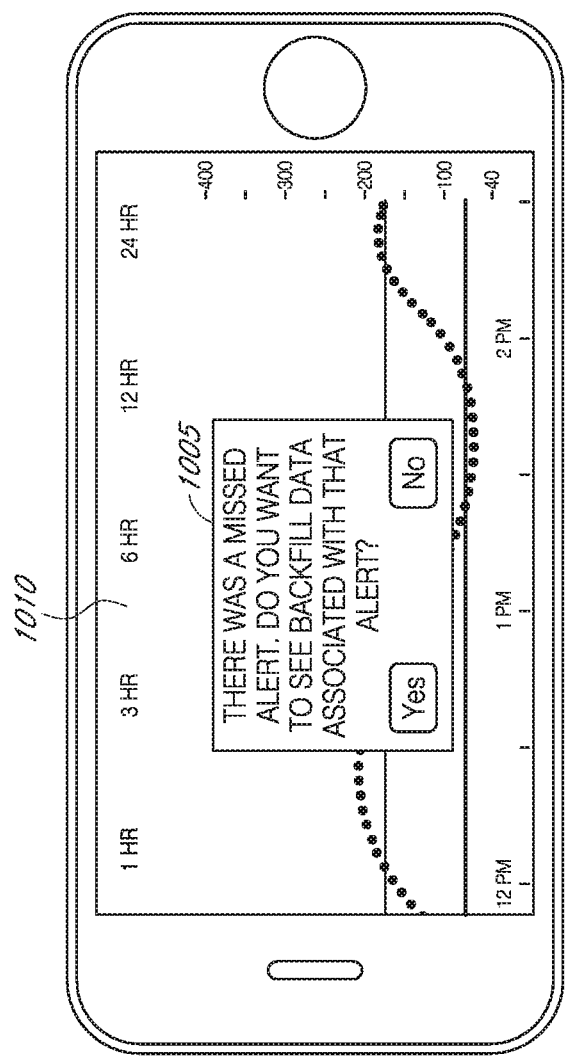
FIG. 10 depicts an example view requesting consent to present backfill data associated with a missed alert, in accordance with some example embodiments.

Referring again to FIG. 4 at 492E, when an alert is missed due to backfill data, the receiver may generate a notification requesting consent to backfilling data, in accordance with some example embodiments. FIG. 10 depicts another example of a view 1010 for presentation at the receiver's user interface. In the example of FIG. 10, the user interface presents a notification regarding a missed alert 1005 and whether the associated backfill data for that alert is to be displayed. If selected, the backfill data is then presented in a graphically distinct way when compared to the non-backfill data.

In some example embodiments, the transmitter may send to the receiver an index of backfill data. The index may be sent when requested by the receiver or at the initiative of the transmitter. The index may include summary information regarding backfill data point(s) for the day (e.g., percentage in range and out of range) that could be displayed to the user if bulk data backfilling were enabled. Bulk data backfilling refers to the transmitter 104 sending to a receiver 110-113 a relatively large block of backfill data. For example, the transmitter 104 may have 6 hours of backfill data to send. When this is the case, the index may prove useful to allow the transmitter to efficiently send the backfill data to the receiver while also sending non-backfill data. The bulk data may be available for the user to view on-demand but not provided and/or displayed automatically. For example, the receiver may request, based on the index, the backfill data or a specific portion of the backfill data.

In some example embodiments, the transmitter may handle the backfill data in a certain way to avoid impacting the more current, non-backfill sensor data. For example, if there is a large amount of backfill sensor data (or an amount over a threshold amount) to send to the receiver, sending all of the backfill sensor data may limit the communication resources available to the more current, non-backfill sensor data (which may cause the user to miss valuable diagnostic information including alerts). In some example embodiments, the backfill sensor data may be prioritized. For example, backfill sensor data that is associated with a missed alert, may be packaged and sent to the receiver before other backfill data.

Referring again to FIG. 4, when the communication link is available again at 410, an evaluation of the missing backfill data may be performed. For example, the evaluation may determine the quantity of missing backfill data that needs to be transmitted. The evaluation may also determine a current glucose state, such as whether the glucose state is normal, hypoglycemic, or hyper-glycemic. Based on the determination(s), the transmitter may determine whether and how the missing data will be backfilled. For example, the transmitter may, based on this determination(s), send more critical (need-to-have data that may be required to make a time sensitive or critical decision regarding an alert) real-time sensor data before any stale backfill data. In some example embodiments, the determination(s) may cause the transmitter to send the backfill data in a certain way. To illustrate further, backfill data may be packaged into smaller data packages that can be transmitted when communication resources are available between the transmitter and receiver. In some example embodiments, the backfill data may be sent in chronological order (for example, most recent backfill data sent before older backfill data). In some example embodiments, the communication link between the transmitter and receiver may allow for a larger window/time to allow for quick data backfilling, when needed based on the above-noted determination(s).

In some example embodiments, the transmitter 104 may be configured to expand the use of the link between the transmitter 104 and receiver 112 for backfilling sensor data, and the transmitter may further be configured to perform the communication expansion when certain conditions are met. For example, when the host user is in a stable glucose region (which can be performed by predicting for example an EGV trend for the time required to perform the transmission), the communication resources available to backfill data transmission may be expanded. On the other hand, if the host user is in a more critical or variable glucose state, less communication resources may be allocated to backfill data (but more may be allocated to non-backfill data). If the host user is in a stable glucose state, an entire block of backfill data may be sent. In this way, backfilling may be performed with less risk of jeopardizing current sensor data and alerts.

In some example embodiments, the sensor data may be stored, at the transmitter 104 or assembly 101, in a database. For example, the database may store sensor data representative of analyte or CGM measurements. These measurements may be stored along with a timestamp indicating when the measurement was made, a glucose value (corresponding to the measurement), a weight indicating how important (for example, actionable or non-actionable) the measurement is, and/or a quantity of times a glucose value has been attempted to be transmitted to a receiver. The transmitter may adjust the weight of the data values based on a variety of factors, so that backfill data with a higher weight can be sent before backfill data with a lower weight. For example, actionable data may be assigned a higher weight when compared to backfill data that is not actionable. Each time the backfill data is sent to a receiver and the transmission fails, the weight may be decreased. Glucose values that are above or below a threshold for an alarm (for example, a glucose high threshold value or a glucose low threshold value) may be adjusted to have a higher weight. Consecutive glucose values that show a rapid rise or fall rate than a threshold rate (in for example mg/dl/min) may be assigned a higher weight. More recent glucose values may be assigned a higher weight than less recent glucose values.

When the transmitter 104 has a transmission window to the receiver 112, the transmitter 104 may obtain one or more packets for transmission. These packets may be obtained by selecting glucose values from the database. Moreover, this selection may take into account the weight (which as noted above may be adjusted up or down based on one or more of the noted factors), time stamp, and/or number of transmission attempts. For example, the transmitter 104 may select the most recent non-backfill data and then select backfill data based on their weight, and then send the selected data to the receiver. In some example embodiments, the receiver selects the backfill data based on a ratio of the weight to the quantity of times the backfill data packet has been sent. The receiver may also maintain a database of glucose values. Each time the receiver receives sensor data packets, the receiver may update its database as well by inserting the received values and time stamps in the database. Redundant sensor data sent by the transmitter may be ignored.

Data backfilling may consume power at the transmitter and/or receiver (which can reduce available battery resources). In some example embodiments, only certain backfill may be sent to the receiver as a way to conserve battery power. In some example embodiments, only certain backfill may be sent to the receiver, when the receiver is operating in a low batter power mode. The selection of which data to send from the transmitter to the receiver may be based on an assessment of the type or importance of backfill data. For example, backfill data for certain types of events or alerts may be sent from the transmitter to the receiver, but other types may not be sent by the transmitter. In some example embodiments, the receiver may be configured to reevaluate its alerts when backfill data is received.

In some example embodiment, battery life may be extended by smartly sending backfill data. For example, the transmitter may send an index or summary of the backfill packets, so that the receiver can selectively request which backfill packets to send. In some example embodiments, the transmission of backfill data may be sent based on the weights or other factors noted above. For example, the weight of the backfill data may take into account whether the backfill data is considered actionable (for example, relevant to the determination of an alert) or non-actionable data. The actionable backfill data may be weighted more heavily, when compared to the non-actionable backfill data. The transmitter 104 may select certain backfill data for transmission to the receiver 112, and this selection may be based on the determined weight or other factors, although the selected backfill packets can be selected in other ways including at random. For example, the transmitter may send non-backfill data and then select 5 backfill data packets at random or select 5 backfill packets that are more heavily weighted as the backfill packets are determined as actionable. In some example embodiments, the receiver 112 may send an acknowledgement message to the transmitter 104. The acknowledgement allows the transmitter to track which packets were successfully received by the transmitter.

Figure 11:
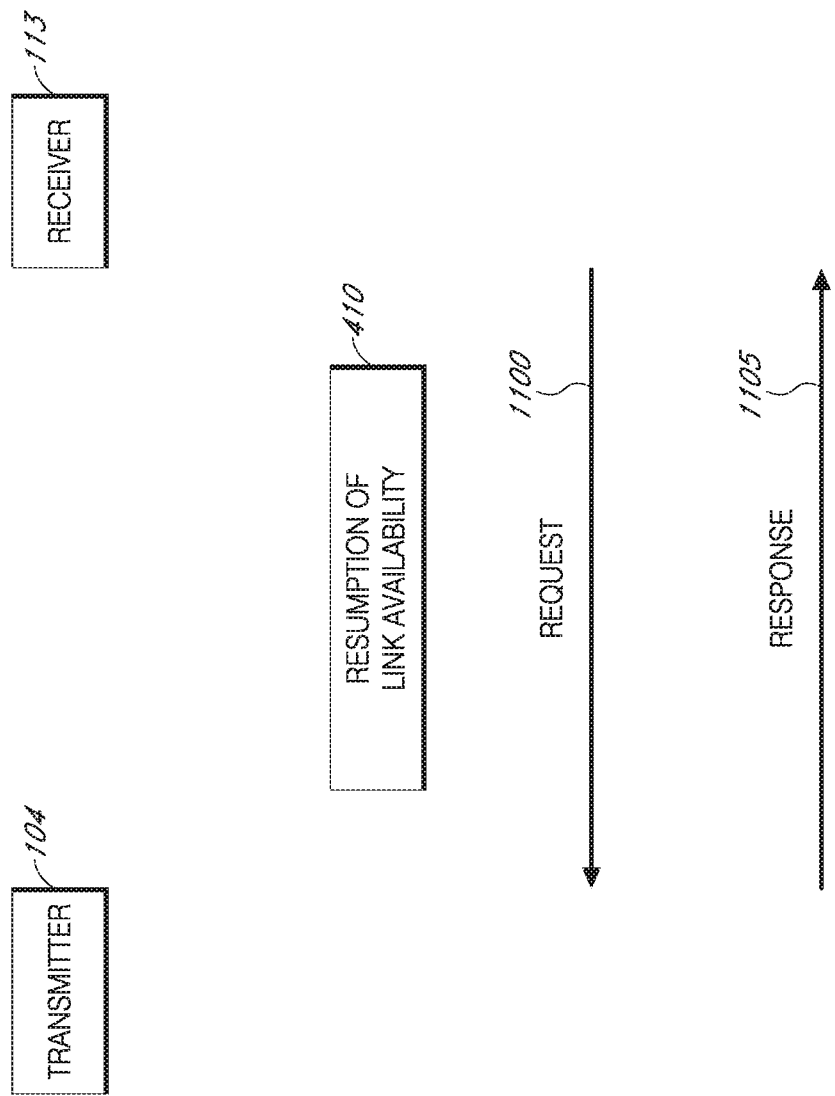
FIG. 11 depicts an example process for requesting backfill data, in accordance with some example embodiments.

FIG. 11 depicts an example process, in accordance with some example embodiments. The description of FIG. 11 also refers to FIGS. 1 and 4.

When there is an error or issue that causes backfill data to be accumulated at the sensor 102/transmitter 104 and the link becomes available again at 410, the receiver may request at 1100 backfill data from the sensor 102/transmitter 104. In some example embodiments, the request may selectively request backfill data to be sent in response 1105. For example, the request 1100 may include an indication (or an index) of specific times where sensor data is missing. In this way, sensor 102/transmitter 104 may respond at 1105 with the backfill data for the requested times (and thus not send the backfill data that is not requested at 1100). In this way, power and/or communication resources may be used more efficiently. Alternatively, the transmitter may just send the last six hours of data, for example, in a single transmission.

In some example embodiments, the request at 1100 may also include a request for missed alerts during the backfill window, in which case the response from the sensor 102/transmitter 104 may include missed alerts (when the transmitter 104 is configured to detect an alert). If alerts were missed, sensor 102/transmitter 104 may respond at 1105 with backfill data. But if no alerts occurred during the backfill time window, sensor 102/transmitter 104 would not provide backfill data at 1105. The sensor 102/transmitter 104 may respond at 1105 with a notification to the receiver that the backfill data was in an allowable range.

In some example embodiments, the request may include an indication to provide a subsample. When this is the case, the sensor 102/transmitter 104 may respond at 1105 with backfill data that has been subsampled (for example, every other data point in backfill data may be sent). Alternatively or additionally, the subsampling may include averaging. For example, the response at 1105 may provide an average backfill data value for a time range (for example, an average EGV data). Moreover, this average EGV may be enabled when there is a stable glucose state in the backfill time window, but disabled if the glucose state is highly variable or the host user is in a more critical glucose state.

In some example embodiments, the request may include an indication to compress. When this is the case, the sensor 102/transmitter 104 may respond at 1105 with backfill data that has been compressed. The compression may comprise a lossless compression that reconstructs the backfill data with little if any measurable loss in fidelity or a lossy compression that provides a less accurate representation of the reconstructed backfill data.

In some example embodiments, backfill data may be compressed, when transmitted. This may save communication resources, as well as reduce power/battery consumption. The compression may be lossless, substantially lossless, or lossy. Moreover, the compression may take the form of subsampling, such as sending only a subset of the sensor data to the transmitter. In some example embodiments, the type of compression may be configurable and the configuration may take into account power availability at the receiver, whether the backfill data is actionable (for example, relates to a current alert or clinical state), a current clinical state of the host-user (for example, if the host is in an alert state, certain backfill data may need to be sent, which might not be the case if the host is normal), clinical relevance of the backfill data, and/or the like. For example, if sensor data or other information relates to actionable, real-time/current data for a patient, this data may be compressed to enable faster transmission for example. Likewise, if sensor data or other information relates to a patient in a certain state, this data may be compressed to enable faster transmission as well. In some example embodiments, compression may be varied based on available power. For example, a more power efficient compression may be used when receiving backfill data, when power is a concern at the receiver.

In some example embodiments, backfill data may be compressed, when transmitted. For example, the backfill data or a plot of the backfill data (or portion of the plot) may be represented by a function, such as a polynomial, transfer function, and/or other expression. Referring to FIG. 5E, the backfill values 555 may represent points on the curve shown. Rather than send the actual backfill data values 555, a function, such as a polynomial, may be generated that represents the portion of the curve at 555. In this example, this representation of the curve 555 may be transmitted rather than the actual, individual data values to provide compression when compared to sending the actual, individual backfill data values 555.

In some example embodiments, the receiver may be used by multiple patients. For example, a clinic may provide the sensor 102/transmitter 104 and receiver 113 to a patient for a certain time. After that time, the sensor 102/transmitter 104 and receiver 113 is returned to the clinic for use by another patient. There could be a problem when data associated with a first patient is stored on the transmitter and later sent to a second patient using the transmitter as backfilled data. This multi-patient use of the same receiver may cause confidentiality as well safety concerns (for example, making a clinical decision based on another patient's data). As such, system 100 may be configured to secure confidential patient data, so that backfill data from a prior patient is not inadvertently shared with another patient that subsequently uses sensor 102/transmitter 104 and receiver 113.

In some example embodiments, backfilling may be limited to a certain time period. The receiver may be configured to allow backfill to be sent to the receiver for a certain time period. Alternatively or additionally, the receiver may be configured allow the backfill to be displayed for a certain period of time. For example, a receiver may be configured to not allow backfill data to be presented during a host patient's bedtime. Alternatively or additionally, backfilling may be limited to only a current session. For example, a session may be defined as a session associated with a given patient. When that session end (for example, if the transmitter is disconnected from the sensor), the session may be terminated. When this is the case, backfilling may cease after the end of the session. Alternatively or additionally, the transmitter may include a smart circuit to detect new sessions (for example, when the transmitter is decoupled from a sensor). In some example embodiments, user data may be saved in the transmitter and tagged with a user ID (or other identifier) specific to each user. The user ID may be patient specific to allow patient-level transmission or deletion of data, when a user mismatch occurs. Alternatively or additionally, backfilling may be disabled altogether in multi-patient settings. For example, the CGM application may be configured for multi-patient use, in which case the backfilling may be disabled to prevent sending from a prior session associated with a prior user.

In some example embodiments, end-user data may be removed from system 100 (including the sensor/transmitter and/or the receiver) when the transmitter is removed from the sensor. The removal may be detected by a smart circuit, an accelerometer, a switch, or other mechanism in the transmitter. The session may also be ended (which would indicate end-user data removal) if the counts representative of transmitter being removed (for example, a small number of glucose value counts may indicate that a transmitter is not attached to the sensor). In the case of a switch, a mechanical switch on the transmitter (where it couples to the sensor) may indicate removal from the sensor, and thus that end-user data should be deleted or not backfilled during a subsequent session.

In some example embodiments, a session identifier may be tied to a user, so when a session ends, the end-user specific patient data is removed or deleted from the sensor/transmitter and receiver, although the end of the session may also trigger deletion of all private patient data. In some example embodiments, a user may be required to enter a patient-specific ID or passcode at the receiver. If this ID or code is not provided, the session ends and the patient-specific data are removed/deleted. In some example embodiments, a delete patient-specific function on the receiver may be implemented to automatically delete patient specific data at system 100. Alternatively or additionally, the backfill module 390 may inhibit the display of any backfill data and/or inhibit use a previous session's data. Alternatively or additionally, a caregiver may configure the receiver and/or transmitter so that backfilled data is not sent/used/displayed. Alternatively or additionally, a password may be used to change this configuration so patient is not able to change it without the caregiver providing the password. Alternatively or additionally, the backfill module 390 may function with only with a certain receiver assigned to a host user for example.

In some example embodiments, a plurality of receivers may be provided with backfill data. When this is the case, a synchronization issue may arise. For example, in a two receiver system, a first receiver may lose a link to the transmitter, while the second receiver maintains the link. In this example, the first and second receivers may be out of synchronization with respect to displayed sensor data.

In some example embodiments, the transmitter may send backfill data to at least one of the plurality of receivers in accordance with process 400 for example. Alternatively or additionally, a receiver may receive backfill data from another receiver. Referring to the first and second receiver example above, the second receiver may provide backfill data to the first receiver, relieving the transmitter of that task. Transmitter may detect that the first and second transmitters are in communication range (e.g., already communicated with the first receiver), in which case the transmitter may indicate to the second receiver to connect with the first receiver to get the backfilled data instead of from the transmitter. Alternatively or additionally, the receivers may detect that they can communicate with one another on their own, and backfill without involvement from the transmitter. If a receiver is sending data to the cloud or server 130, the cloud or server 130 may backfill the other receiver(s) as well. In some example embodiments, a so-called remote follower at remote computer 145A or B may access server 130 at FIG. 1 to obtain CGM sensor data for a host-patient's receiver. For example, a parent, caregiver, and/or the like may also receive, for a given user at a receiver, CGM data, alerts, notifications, and/or the like. In this way, the remote follower may also monitor the glucose state of the host-patient at the receiver.

In the case of backfill, when a remote follower is tracking a host-patient at a receiver through the cloud/server 130, issues may arise and, in particular, issues may arise when a communication link between transmitter and receiver and/or when a communication link between the receiver and cloud/server 130 is lost and/or communication link between the cloud/server 130 and remote monitor is lost. For example, the remote follower may receive an alert about a hypo-glucose level or hyper-glucose level at certain time, but that may be due to backfill data (so the alert may not be current and thus not need to be acted upon if the host's glucose condition has changed for example). The remote follower may not receive the alert but instead may not understand why an alert was not received given the data received by the remote follower. Moreover, the remote follower may have no clue as to whether the communication link between transmitter and receiver was lost (which may be of greater concern) or the communication link between the receiver and cloud/server 130 is lost (which may be of less concern).

In some example embodiments, the remote follower may receive backfill data, and that backfill data may be graphically distinct from non-backfill, received in real-time data as described herein. Alternatively or additionally, the remote follower may receive backfill data, and the backfill data may include an indication or notification regarding which link was unavailable (for example, the transmitter to receiver link, or some other link after the receiver).

In some example embodiments, the remote follower may also present at a user interface the backfill data and non-backfill data with an indication of where the link failure occurred, such as whether the first link between the transmitter and receiver failed, the second link between receiver to server failed, and/or the third link between the server and remote follower failed. For example, the indication may include different graphical indicators, notification messages, and/or the like. Moreover, backfill data associated with the first link may be indicated in a graphically distinct way from data losses caused by the noted second or third links. In this way, the remote follower can graphically assess whether the first link between the transmitter and receiver failed which is more of a concern than the other two links.

In some example embodiments, a remote follower's receiver/display may present an alert with an indication of backfilling to indicate to the remote follower that the alert was missed but it was due to backfilling (communication loss) rather than for some other reason. In some implementations, the types of alerts sent to a remote follower may be different from the types of alerts triggered at the receiver 110-113.

In some example embodiments, if the remote server has not received any data from the receiver over a certain time, the server 130 may send to the remote follower an alert message for display. This alert message may indicate that there may be a communication link outage between the receiver and server 130. In response, the remote follower can assess the criticality of the situation, such as a missed alert.

In some example embodiments, the graphically distinct indication of backfill data (to distinguish it from non-backfill data) may be based on time of day. For example, when a user is sleeping, the user should be made aware the data was not being received by his/her alerting receiver, while sleeping to enable a possible remedy. Moreover, the receiver 110-113 may require a host patient to perform an acknowledgement (for example, perform a selection at a user interface display at the receiver) of backfilling, when backfilled data is received at night.

In some example embodiments, the receiver may generate predicted data (for example, based on a moving average or the like). The predicted data may be used at the receiver until backfill data is received at the receiver. The predicted data may be used to fill in gaps of data, such as relatively short gaps in the data. In some example embodiments, predicted data may be displayed at the receiver in a graphically distinct way so that it can be distinguished from other types of data, such as backfill data and/or non-backfill data, although the predicted data may be presented in the same manner as backfill data and/or non-backfill data. As noted, in some example embodiments, backfill data may be presented at the receiver with an indication that the sensor data is backfill, while in some other embodiments, backfill data may be presented at the receiver without an indication. For example, if the time period associated with the backfill data is relatively short (for example, less than a predetermined time or less than a predetermined quantity of data points), the receiver may be configured present the backfill data without an indication that the sensor data is backfill.

In some example embodiments, the backfill mode configuration may be dependent on whether the receiver is associated with a role of the user, such as whether the user is a host-patient or a remote follower. For example, the host user may view a graphic indication for backfill data associated with the transmitter to receiver link, but the view presented at the remote follower may graphically show backfill data caused by other links as well, such as the receiver to server link or server to remote follower link.

In some example embodiments, the receiver may directly communicate with a remote follower (for example, the remote follower's display device or receiver) and backfill any data missing at the remote follower.

In some example embodiments, the graphically distinct backfill indication may be presented in some display screens but not others. For example, backfill may not be indicated as backfill on certain types of screens, while other types of screens may indicate whether the sensor data is backfill.

Figure 12:
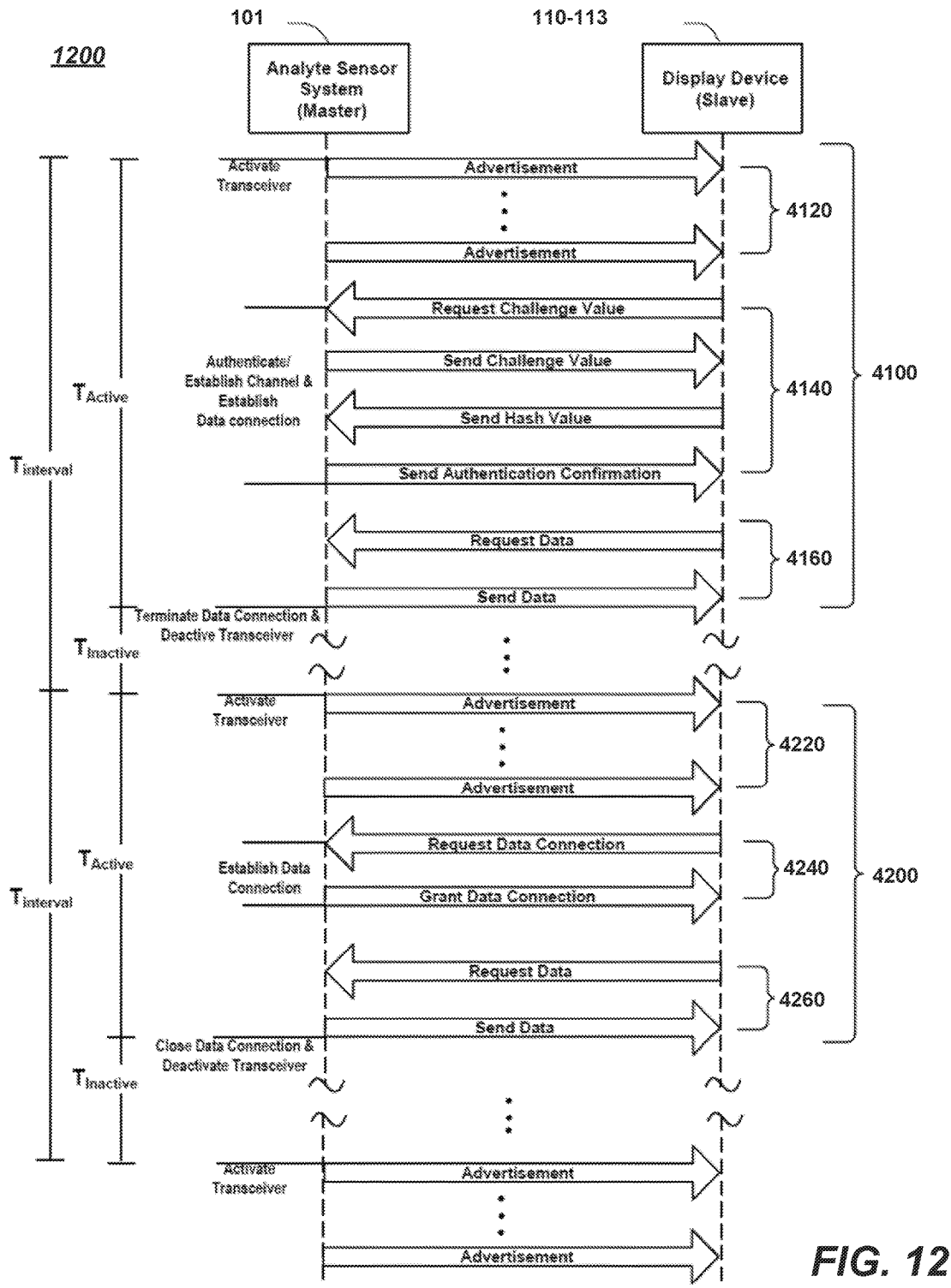
FIG. 12 depicts an example process for a wireless data communication protocol between an analyte sensor system and a display device, in accordance with some example embodiments.

FIG. 12 depicts an example of a process 1200 between an analyte sensor system and a display device, in accordance with some example embodiments. The description of process 1200 also refers to FIG. 1.

The process depicts an analyte sensor system, such as sensor assembly 101 (which includes the transcutaneous analyte sensor 102 and the transmitter/sensor electronics unit 104 for wirelessly transmitting analyte information to a receiver, such as display device 110-113).

In the examples described below, the analyte values are glucose values based on one or more measurements of glucose level by the analyte sensor 101 for illustration purposes. However, it should be understood that the analyte values can be any other analyte value described herein including backfill data, private data, and/or the other types of data. The wireless data communication between the analyte sensor system 101 and the display device may happen periodically, at times separated by an update interval denoted "Ti a" that may correspond to a time duration between two consecutive wireless communication sessions between the transceiver 104 of the analyte sensor system 101 and a corresponding transceiver of the display device 110-113. Alternatively, the update interval may be thought of as a period of obtaining and sending a recently measured glucose value. Transmitting advertisement signals, establishing a data connection (e.g., a communication channel), and requesting and sending data may occur during wireless communication sessions each lasting an active time or period denoted "$T_{Active}$" within an update interval $T_{interval}$. In between two consecutive wireless communication sessions, the transceiver 316 goes into an inactive or sleep mode for an inactive period denoted as "$T_{Inactive}$" to conserve battery life and/or reduce peak voltage requirements, for example.

FIG. 12 shows two such wireless communication sessions, namely, a first wireless communication session 4100 and a second wireless communication session 4200. Each wireless communication session 4100, 4200 starts with the analyte sensor system 101 establishing a data connection with at least one display device 110-113. To establish a data connection with the display device, the transceiver 104 of the analyte sensor system 101 transmits a series of advertisement signals 4120 during the first wireless communication session 420. Each advertisement signal may be considered an invitation for a display device 110-113 to establish a data connection with the transceiver 104. The data connection may be carried by one or more wireless links, and these links may be in accordance with a radio technology such as Bluetooth, Bluetooth Low Energy, NFC, WiFi, cellular, and/or other types of radio technologies. In the case of Bluetooth and Bluetooth Low Energy, the sensor system 101 and receiver such as display 110-113 may operate using less energy, when compared to WiFi, cellular, and/or other longer range radio technologies.

In the illustrated example of FIG. 12, the analyte sensor system 101 may need to engage in an initial system setup as the system 101 may have been just turned on for the first time and/or may not be currently paired with a display device 110-113. The user of the display device 110-113 identifies a new or never-been used analyte sensor system 101 that needs to be paired with the display device by entering identification information (e.g., a serial number) associated with the new/unpaired analyte sensor system 101 via a custom application running on the display device using a user interface (e.g., a touchscreen display). During the first wireless communication session 4100, an authentication procedure may be performed as part of a data connection process 4140. To establish a data connection with the analyte sensor system 101, the display device 110-113 may listen continuously until an advertisement signal transmitted by the transceiver 104 of the analyte sensor system 101 is received. Once the analyte sensor system's 101 transceiver 104 begins transmitting advertisement signals 4120, it may take one, two, or more advertisement signals for the display device 110-113 to receive the advertisement signal and responds to the advertisement signal. In some embodiments, the transceiver 104 stops sending additional advertisement signals once a display device receives an advertisement signal and responds to the advertisement signal, for example, via an acknowledgement. In other embodiments, the analyte sensor system's 101 transceiver 104 may continue to send additional advertisement signals even after receiving a response from a display device so that another display device may receive and respond to one of the additional advertisement signals.

After an advertisement signal is successfully received by a display device 110-113, the display device and the analyte sensor system 101 engage in a first data connection process 4140. During the first data connection process 4140, the display device requests a challenge value from the analyte sensor system 101 and the analyte sensor system 101 sends the change value to the display device in response. Upon receiving the challenge value, the display device 110-113 calculates a hash value based on the challenge value and the identification information associated with the analyte sensor system 101 and/or the transceiver 104, and then responds by sending the hash value to back to analyte sensor system's transceiver 104. The analyte sensor system's transceiver 104 receives the hash value from the display device 110-113, decodes the identification information from the hash value, and verifies that the received identification information matches identification information associated with the sensor system 101 and/or transceiver 104 previously stored in the memory of the analyte sensor system 101, such as during manufacturing of the sensor system 101. Upon verification, the transceiver 104 sends a signal confirming a successful authentication to the display device 110-113. Once authenticated, the analyte sensor system 101 and display device 110-113 may exchange information to determine how data will be exchanged (e.g., a specific frequency, time slot assignment, encryption, etc.).

After completion of the first data connection process 4140, the analyte sensor system 101 and the connected at least one display device 110-113 may engage in a first data communication 4160 during which the connected display device can request and receive desired information (e.g., analyte data, control information, identification information, backfill data, private data (which may be associated with a data manifest and/or encryption information), instruction(s), and/or the like) from the analyte sensor system 101. When the first data communication 4160 is completed, the data connection is terminated (e.g., by closing the established communication channel) and the transceiver 104 (and/or a corresponding transceiver at a display device 110-113) can be deactivated by causing the transceiver 104 (or processor and/or other circuitry associated with sensor system 101) to enter a lower power mode, such as a sleep mode or inactive mode. In some embodiments, the transceiver 104 is completely powered down during a sleep mode. In other embodiments, the transceiver 104 is in a low power mode using only a small fraction (e.g., 1-10%) of the normal current/power.

In some example embodiments however, the data transmission at 4160 may not occur or may be interrupted for a variety of reasons. For example, the analyte sensor system 101 may not be able to successfully transmit data to the receiver due to a failure or error in any portion of the protocol such as an error/failure in the advertisement process 412, an error/failure in the authentication 414, and/or the like. When this is the case, the analyte sensor system 101 may store analyte data as backfill data. As such, when another wireless session and data session allow for data transfer, the analyte sensor system 101 may send at 4160/4260 ("send data") to the receiver, such as display device 110-113, the backfill data as well as non-backfill data. Moreover, the backfill data may be sent as noted above (e.g., as a user definable option, in reverse chronological order, send non-backfill data transmission before backfill data transmission, backfill data transmission before non-backfill data transmission, and more recent backfill data may be transmitted more frequently when compared older, backfill data).

In some example embodiments, one or more of the advertisement messages at 4120/4220 may be used to carry backfill data, non-backfill data, and/or private data. The advertisement messages may be used alone or in combination with the sending at 4160/4260. In some examples, the above-mentioned data may be encrypted in the advertisement messages and/or in the sending at 4160/4260.

To illustrate further, the analyte sensor system may, at 4120, transmit at least one advertisement at a certain time, in accordance with some example embodiments. Furthermore, the analyte sensor system may, at 4160, receive a data connection request from a user equipment, such as display device(s) 110-113, at a certain time, and then establish, at 4160, a data connection with the user equipment, in accordance with some example embodiments. The analyte sensor system may via the established data connection transmit an analyte value to the user equipment. However, when there is an error (e.g., due to an error in the advertising process, data connection establishment process, authentication process, and/or any other reason that causes the analyte sensor system from successfully transmitting to the user equipment non-backfill data), the analyte sensor system may store analyte data as backfill, so that the stored backfill data can be transmitted at another time when a data connection is established.

The active period $T_{Active}$ corresponding to a duration of each wireless communication session may be a small fraction of the update interval $T_{interval}$ corresponding to a period between two consecutive wireless communication sessions. For example, $T_{interval}$ may be between about 200 and 400 seconds and $T_{Active}$ may be between 20 and 40 seconds. As such, the transceiver 104 of the analyte sensor system 101 may be powered fully for only 10 percent (e.g., 30 seconds) of a five minute $T_{interval}$. This may significantly reduce power consumption and peak voltage demand. In some cases, the transceiver 104 is not completely powered down, but enters a low-power mode when not transmitting.

After an inactive time or period $T_{Inactive}$, a second wireless communication session 4200 may start when the analyte sensor system's transceiver 104 (and the corresponding transceiver at a display device) powers up again, begins transmitting a second series of advertisement signals 4220, engages in a second data connection process 4240 and a second data communication process 4260 with a transceiver of a display device 110-113 as shown in FIG. 12.

Unlike the first data connection process 4140, however, the second data connection process 4240 may not involve an authentication because the analyte sensor system 101 and the display device 110-113 have been successfully paired or bonded during the first wireless communication session 410 as described above. This process may continue, with new data connections and communications being completed at the pre-determined intervals. During all or part of each inactive period $T_{Inactive}$ during which the analyte sensor system's transceiver 104 is in a sleep mode, the processor 314 can take measurement(s) of one or more analyte values using the analyte sensor 101 and the sensor measurement circuitry 102. For example, a processor at system 101 may take multiple analyte value measurements and average them to generate a single averaged analyte value to be transmitted in a next wireless communication session.

Continuously re-establishing a new communication channel to allow for partially or wholly powering down the transceiver 104 during each update interval $T_{interval}$ can provide significant power savings and can allow the sensor electronics module 102 (FIG. 1) to operate continuously for six months or more without requiring a battery replacement. Furthermore, rather than blindly transmitting glucose data points during the update interval $T_{interval}$, establishing specific data connections (e.g., communication channels) with only the desired display devices 110-113 can prevent unauthorized use and interception of glucose measurement values. In some embodiments, only a subset of multiple display devices 110-114 can be configured to receive different data such as glucose measurement values and/or alarm conditions. This may have a benefit of preventing multiple display devices from issuing alarms, thereby confusing and/or frustrating the user. In addition, by establishing a secure two-way communication channel, requests for specific glucose measurement values or communication of calibration or configuration information may be transmitted on an as-needed/requested basis between the analyte sensor system 101 and display device 110-114.

Furthermore, in some embodiments, the transceiver 104 may not be activated for data communication every update interval $T_{interval}$. Instead, the transceiver 104 may be activated every second, third or fourth update interval $T_{interval}$, for example, so that communication between the analyte sensor system 101 with the display device 110-113 occurs less frequently than every update interval $T_{interval}$. Doing so can further reduce power consumption. Activation could also depend on the sensor data. For example, only activate the transceiver if data meets certain thresholds, such a current rate of change, current high value, current low value, absolute difference from a previously exchanged value, percentage difference from a previously exchanged value, and the like. In some embodiments, instead of skipping certain fixed update intervals, the length of each interval can be made vary based on sensor data. For example, if the sensor data indicates a low glucose value and/or a hypoglycemic reaction is detected, the update interval value can be shortened from a normal update interval value so that readings that are more frequent are taken and transmitted.

In some embodiments, the update interval $T_{interval}$, the active period $T_{Active}$ and a frequency $F_{Activation}$ by which the transceiver is activated (e.g., every second, third or fourth update interval) may be variable. In some embodiments, the above-identified parameters can be user configurable (e.g., by inputting a value for the variable using user interface of display device 110-113) and/or automatically varied by the analyte sensor system 101 or display device 110-113 based on one or more criteria. The criteria may include: (i) a monitored battery power of the sensor system 101, (ii) a currently measured, previously measured and/or predicted glucose concentrations meeting or exceeding a predetermined threshold, (iii) a glucose concentration trend of the host based on currently measured, previously measured and/or predicted glucose concentrations, (iv) a rate of change of glucose concentration of the host based currently measured, previously measured and/or predicted glucose concentrations meeting or exceeding a predetermined threshold, (v) whether the host is determined to be in or near hyperglycemia based on currently measured, previously measured and/or predicted glucose concentrations, (vi) whether the host is determined to be in or near hypoglycemia based on currently measured, previously measured and/or predicted glucose concentrations, (vii) user inputted activity of the host (e.g., exercising or sleeping), (viii) time since a sensor session has started (e.g., when a new sensor 10 is used), (ix) one or more errors detected by sensor system 101 or display device 110-113, and (x) type of display device.

$T_{interval}$, $T_{Active}$, $F_{Activation}$ and/or other configuration items described herein may form part of a communication protocol profile that may be stored on any device that implements the fundamental communication protocol to allow for a customized use of the protocol for communicating analyte measurement values in the analyte sensor system 101 and display device 110-113.

In some example embodiments, there may be provided a protocol that may enable a sensor system 101 to encrypt and then transfer private data to a receiver, such as a display 110-113. This private data may then be stored at the receiver and forwarded to server 130, where the private data can be decrypted and processed. The private data may correspond to analyte sensor data measured by the sensor system 101, such as raw counts, or raw sensor data. In some examples, private data may include, but not limited to, sensor information associated with the sensor 102, battery information of the transmitter/sensor electronics 104, calibration information, manufacturing information, algorithm records, and the like. For example, sensor information may include sensor identification information, operational information of the sensor, and other sensor related information. Battery information may include operational information of the battery, such as a profile of the battery and the like. As described herein, private data may be encrypted or encoded private data and may include one or a combination of the above-mentioned private data. As further described herein, in some example embodiments, private data may be transmitted by the transmitter either individually, or in combination with other data such as non-backfill data and/or backfill data (e.g., when the backfill data is not included as private data).

Figure 13:
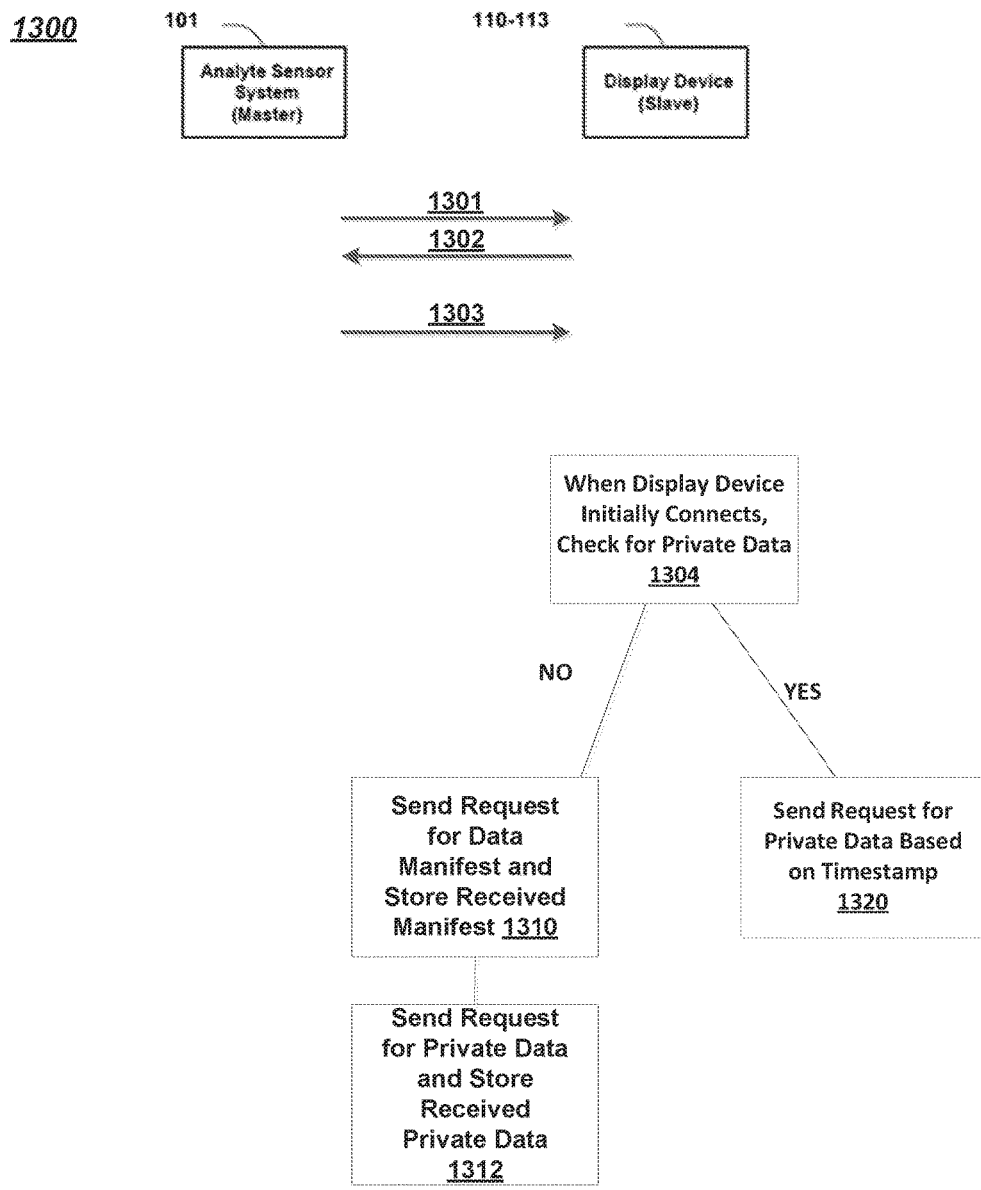
FIG. 13 depicts an example of a process for handling data including private data, in accordance with some example embodiments.

FIG. 13 depicts a private data transfer process 1300, in accordance with some example embodiments. The description of process 1300 also refers to FIGS. 1 and 12.

In some example embodiments, the sensor system 101 may send, at 1301, an indication to a display device 110-113. This indication may signal to the display device that the sensor system 101 has data, such as such as private data, EGV, backfill data and/or the like, to send to the receiver or another device, such as server 130. The display device 110-113 may send a request, at 1302, the sensor system 101 to provide certain data. For example, the display device may request the sensor system 101 to provide certain data, such as private data, EGV, or backfill data (which may have been missed by the display device). In the case of private data, the sensor system 101 may send private data to the display 110-113 in an encrypted form, so that the display device cannot read the contents of the private data. The display device may store the private data, and the display device may later forward (or relay) the encrypted data to other device such as server 130 which may have the appropriate encryption keys to decrypt the private data for the user of sensor system 101. It is contemplated that, in some example embodiments, the private data may be forwarded or relayed by the display device periodically (e.g., every six hours) to the server 130. Furthermore, the forwarding may be based on a timestamp of the private data, for example, oldest private data may be forwarded prior to the newest private data or in a reverse chronological order.

As noted, the private data may be considered private in the sense that it may be encoded, such as by encryption, when sent to a receiver, such a display devices 110-113, server 130, and/or other devices. The system 101 may map private data to a data manifest describing how to handle (e.g., parse, interpret, and/or the like) the corresponding private. Moreover, the private data and manifest data may also be mapped to encryption information, such as a public key, key identifier, and/or the like.

At 1303, the system 101 may send data, such as private data, manifest information, and encryption information to a receiver, such as display device 110-113 where the data can be stored (although other types of data may be sent as well). The sending at 1303 may be in accordance with the data send 4160/4260 described above with respect to FIG. 12, although the private data, manifest information, and encryption information may be sent in other ways as well. The data transmission from the system 101 may be initiated by the system 101 or may be in response to the request 1302 from a receiver, such as at least one of the display devices 110-113.

In some example embodiments, when a display device 110-113 connects to an analyte sensor system 101 for the first time (see, e.g., 4100 described above), the display device 110-113 may, at 1304, query a database to determine whether there is private data from this new analyte sensor system 101.

If a display device 110-113 does not have private data for the analyte sensor system 101 (e.g., as evident from not having an a private data database entry for the new analyte sensor system 101), the display device 110-113 may, at 1310, request from the analyte sensor system 101 a data manifest and then store the received data manifest. For example, the request for the data manifest may be performed in accordance with the data request 1302 and the received data may be as noted at 1303.

At 1312, the display device 110-113 may request private data from the analyte sensor system 101, and then store the private data returned by the new analyte sensor system 101 in response to the request. In some example embodiments, the request may indicate a time frame for which the private data is requested. For example, the request may indicate that the prior 11 days' worth of private data is requested, although other amounts may be requested as well. The request for the private data may be performed in accordance with the data request 1302 and the received data may be as noted at 1303.

If a display device 110-113 does have private data for the new analyte sensor system 101 (e.g., as evident from having a private data database entry for the new analyte sensor system 101), the display device 110-113 may, at 1320, may use the last recorded timestamp (associated with system 101) to request private data starting from that timestamp. In some example embodiments, if the timestamp is older than a certain time, the display device 110-113 may disregard the timestamp and request private data for a given time frame (e.g., 11 days as noted above). The request for the private data may be performed in accordance with the data request 1302 and the received data may be as noted at 1303.

To illustrate further, a user equipment, such as at least one of display devices 110-113, may transmit a data connection request to the analyte sensor system 101, so that a data connection request is established with the analyte sensor system. In some example embodiments, the user equipment (e.g., one of the display devices 110-113) may check for private data that is stored at the user equipment and that is associated with the analyte sensor system with which a data connection has been established. When the checking identifies private data associated with the analyte sensor system, the user equipment may request private data from the analyte sensor system. However, when the checking does not identify private data associated with the analyte sensor system, the user equipment may request, from the analyte sensor system, manifest data for the private data, and then request, in response to receiving the manifest data, private data from the analyte sensor system. The user equipment may also receive the requested private data to enable storage before forwarding to a server.

In some example embodiments, the receiver may send a request for private data (and the corresponding data manifest and/or encryption information), and this request may include a predetermined format. For example, the request may be implemented as a data set stream request (DataSetStreamRequest). Moreover, the request for private data (and the corresponding data manifest and/or encryption information) may be performed from time to time (for example, every 30 minutes, although other times may be configured at the receiver as well). When the sensor system 101 is, for example, out of range of the receiver, such as display device 110-113) for the request for private data, the receiver may send another request at another time (e.g., during the next connection or after another predetermined time).

In some example embodiments, the request may explicitly have a field or filter requesting the data manifest (e.g., the dataSetFilterType may be set to ManifestInfo (1) within the DataSetStreamRequest). In some example embodiments, the data manifest may include the version or revision of the manifest, how many "DataSetTypes" exist and whether the data sets are encrypted, and how many partitions (or types) are in the transmitters database, the revision of the partition, and the length of the record in the partition.

In some example embodiments, the request may explicitly have a field or filter requesting the encryption information (e.g., dataSetType set to TransmitterEncyrptionInfo (2) within the DataSetStreamRequest).

To request the private data from the sensor system 101, the receiver, such as display device 110-113, may send a request, such as a DataSetStreamRequest configured as follows:
  dataSetType shall be set to TransmitterPrivateData (1).
  dataSetFilterType shall be set to InRangeInclusive (2).
  param1=Start Transmitter Time (time from when to start transfer, max number or days or time frame).
  param2=Current Transmitter Time.
  param3=Max number of bytes per stream (based off receiver constraints).

When the sensor system 101 receives the request for private data (which may also request a data manifest and/or encryption information), the sensor system 101 may generate a new data stream by sending data over an "Exchange Variable Characteristic" using notification messages, such as Bluetooth Low Energy notifications in 20 byte packets (e.g., a DataSetStreamPacket). The first 2 bytes of each 20 byte packets will be used to convey a packetNumber and streamId. The packet number may start at 0 at the beginning of every stream and increment per packet. The packet number may be the first 14 bits of these first 2 bytes. The stream ID may be used to ensure the packets being received by the receiver 110-113 belong to the same stream. The stream ID may be the last 2 bits of these first 2 bytes. The last 18 bytes may be assigned to payload data. The total number of 20 byte packets per stream will be determined by the value specified in field "param3" by the receiver in the request. After the final packet in the stream is received, the sensor system 101 may send a response (DataSetStreamResponse) including an appropriate opcode and transmitter status. For example, the DataSetStreamResponse may include:

Stream status code;
Reiterate the stream ID that this response corresponds to;
Time stamp of the first record in the group (oldest);
Time stamp of the last record in the group (newest);
Total number of payload bytes that were sent in the corresponding stream;
Cyclic Redundancy check (CRC) of the stream data; and
CRC of the response.

In some example embodiments, the request for a data manifest may be performed when a receiver such as display 110-113 and a sensor system 101 have an initial wireless session such as session 4100. The data manifest may describe the data that will be received on the stream from the sensor system 101. In the case of private data, a display device may not actually care what is in the manifest information, it just needs to be enough for the downstream consumers (e.g., a server) to parse the private data that will arrive on the stream. The data manifest may indicate type, revision, and length as noted. Moreover, if the stream is encrypted, the data manifest may also indicate the encryption.

In some example embodiments, a display device 110-113 may send request 1302 as a write with acknowledgement. The request may indicate a time frame (e.g., start and stop time) for the requested data and/or a limit on how many bytes can be transferred to the display device. The sensor system 101 may respond at 1303 by first starting the data stream using an event notification message. Next, the sensor system may find the first record in its partitions with the lowest timestamp (representing the oldest data) and streams this lowest time stamp in the notification message. This record may immediately follow the previous byte of the last record. There may be no padding in any of the stream packets to fill to the end of the buffer. This may be repeated until the requested time span has been reached or the data byte limit specified in the request has been reached. In some example embodiments, if a single record cannot be transferred due to the hard byte limit being too small, an error is thrown. Once the stream of records is complete, a message may be sent to the display device 110-113. The message may include transmitter time of the first record in the stream, transmitter time of the last record in the stream; total quantity of packets transferred; and/or the cyclic redundancy check (CRC) across the entire stream. If a display requested a range of data larger than could be transferred with a recommended soft limit, the display may trigger a new request using (the transmitter time of the last record on the previous stream+1 second for example) as the new lower bound.

Exemplary Methods, Storage Media, and Apparatus

Any of the features of the following ninety six exemplary methods, storage media, and apparatus is applicable to all aspects and embodiments identified herein, including other of the ninety six exemplary methods, storage media, and apparatus. Moreover, any of the features of the following ninety six exemplary methods, storage media, and apparatus is independently combinable, partly or wholly with other aspects and embodiments described herein in any way, e.g., one, two, or three or more embodiments may be combinable in whole or in part, including in connection with any of the ninety six exemplary methods, storage media, and apparatus. Further, any of the features of the following ninety six exemplary methods, storage media, and apparatus may be made optional, including to other of the ninety six exemplary methods, storage media, and apparatus. Any aspect or embodiment of a method can be performed by a system or apparatus of another aspect or embodiment, and any aspect or embodiment of a system or apparatus can be configured to perform a method of another aspect or embodiment, including in connection with ninety six exemplary methods, storage media, and apparatus.

Exemplary Method No. 1

A method comprising: receiving, at a receiver, backfill data representative of sensor data stored, at continuous blood glucose sensor and transmitter assembly, due to a loss of a wireless link between the receiver and the continuous blood glucose sensor and transmitter assembly; generating, at the receiver, at least one of a notification or a graphically distinct indicator for presentation at a display of the receiver, the at least one of the notification or the graphically distinct indicator enabling the backfill data to be graphically distinguished, when presented at the display, from non-backfill data; and generating, at the receiver, a view including the backfill data, the non-backfill data, and the generated at least one of the notification or the graphically distinct indicator.

Exemplary Method No. 2

The method of Exemplary Method No. 1, wherein the graphically distinct indicator comprises a color that is different from another color used to present the non-backfill data.

Exemplary Method No. 3

The method of any of Exemplary Method Nos. 1 through 2, wherein the graphically distinct indicator comprises a symbol that is different from another symbol used to present the non-backfill data.

Exemplary Method No. 4

The method of Exemplary Method No. 3, wherein the symbol comprises at least one of a dashed line, a solid line, a solid polygon, or a hollow polygon.

Exemplary Method No. 5

The method of any of Exemplary Method Nos. 1 through 4, wherein the graphically distinct indicator comprises an overlay on the backfill data.

Exemplary Method No. 6

The method of any of Exemplary Method Nos. 1 through 5, wherein the notification comprises an indication that the non-backfill data is being presented at the display.

Exemplary Method No. 7

The method of any of Exemplary Method Nos. 1 through 6, wherein the notification indicates at least one alert occurring during a time associated with the backfill data.

Exemplary Method No. 8

The method of any of Exemplary Method Nos. 1 through 7, wherein the notification indicates a request to display the backfill data associated with a missed alert.

Exemplary Method No. 9

The method of any of Exemplary Method Nos. 1 through 8, wherein the notification indicates a request to consent to the display of the backfill data.

Exemplary Method No. 10

The method of any of Exemplary Method Nos. 1 through 9, wherein the notification indicates a request to consent to the display of the backfill data and at least one alert occurring during a time associated with the backfill data.

Exemplary Method No. 11

The method of any of Exemplary Method Nos. 1 through 10, wherein the notification indicates a request to display backfill data, when an alert is missed.

Exemplary Method No. 12

The method of any of Exemplary Method Nos. 1 through 11, wherein the view includes a plot of glucose values formed from the backfill data and the non-backfill data.

Exemplary Method No. 13

The method of any of Exemplary Method Nos. 1 through 12, further comprising: displaying, at the receiver, the view including the backfill data, the non-backfill data, and the generated at least one of the notification or the graphically distinct indicator.

Exemplary Method No. 14

The method of Exemplary Method No. 13, wherein the backfill data is displayed, when an indication of consent is received.

Exemplary Method No. 15

The method of any of Exemplary Method Nos. 1 through 14, further comprising: inhibiting, at the receiver, the receiving of the backfill data, without an indication of consent.

Exemplary Method No. 16

The method of any of Exemplary Method Nos. 1 through 15, wherein the receiving is in response to a request from the receiver.

Exemplary Method No. 17

The method of any of Exemplary Method Nos. 1 through 16 further comprising: classifying, at the receiver, an alert as a missed alert, when the alert occurred during a time associated with the backfill data.

Exemplary Method No. 18

The method of any of Exemplary Method Nos. 1 through 17, wherein the backfill data is received as compressed data.

Exemplary Method No. 19

The method of Exemplary Method No. 18, wherein the compressed data comprises a function representative of at least a portion of a curve corresponding to the backfill data.

Exemplary Method No. 20

The method of any of Exemplary Method Nos. 1 through 19, wherein the receiving comprises: receiving, at the receiver, more recent backfill data is received more frequently, when compared to older backfill data.

Exemplary Apparatus No. 21

An apparatus comprising: at least one processor; and at least one memory including computer program code which when executed causes operations comprising: receiving, at the apparatus, backfill data representative of sensor data stored, at continuous blood glucose sensor and transmitter assembly, due to a loss of a wireless link between the apparatus and the continuous blood glucose sensor and transmitter assembly; generating, at the apparatus, at least one of a notification or a graphically distinct indicator for presentation at a display of the apparatus, the at least one of the notification or the graphically distinct indicator enabling the backfill data to be graphically distinguished, when presented at the display, from non-backfill data; and generating, at the apparatus, a view including the backfill data, the non-backfill data, and the generated at least one of the notification or the graphically distinct indicator.

Exemplary Apparatus No. 22:

The apparatus of Exemplary Apparatus No. 21, wherein the graphically distinct indicator comprises a color that is different from another color used to present the non-backfill data.

Exemplary Apparatus No. 23:

The apparatus of any of Exemplary Apparatus Nos. 21 through 22, wherein the graphically distinct indicator comprises a symbol that is different from another symbol used to present the non-backfill data.

Exemplary Apparatus No. 24:

The apparatus of any of Exemplary Apparatus Nos. 21 through 23, wherein the symbol comprises at least one of a dashed line, a solid line, a solid polygon, or a hollow polygon.

Exemplary Apparatus No. 25:

The apparatus of any of Exemplary Apparatus Nos. 21 through 24, wherein the graphically distinct indicator comprises an overlay on the backfill data.

Exemplary Apparatus No. 26:

The apparatus of any of Exemplary Apparatus Nos. 21 through 25, wherein the notification comprises an indication that the non-backfill data is being presented at the display.

Exemplary Apparatus No. 27:

The apparatus of any of Exemplary Apparatus Nos. 21 through 26, wherein the notification indicates at least one alert occurring during a time associated with the backfill data.

Exemplary Apparatus No. 28:

The apparatus of any of Exemplary Apparatus Nos. 21 through 27, wherein the notification indicates a request to display the backfill data associated with a missed alert.

Exemplary Apparatus No. 29:

The apparatus of any of Exemplary Apparatus Nos. 21 through 28, wherein the notification indicates a request to consent to the display of the backfill data.

Exemplary Apparatus No. 30:

The apparatus of any of Exemplary Apparatus Nos. 21 through 29, wherein the notification indicates a request to consent to the display of the backfill data and at least one alert occurring during a time associated with the backfill data.

Exemplary Apparatus No. 31:

The apparatus of any of Exemplary Apparatus Nos. 21 through 30, wherein the notification indicates a request to display backfill data, when an alert is missed.

Exemplary Apparatus No. 32:

The apparatus of any of Exemplary Apparatus Nos. 21 through 31, wherein the view includes a plot of glucose values formed from the backfill data and the non-backfill data.

Exemplary Apparatus No. 33:

The apparatus of any of Exemplary Apparatus Nos. 21 through 32, further comprising: displaying, at the apparatus, the view including the backfill data, the non-backfill data, and the generated at least one of the notification or the graphically distinct indicator.

Exemplary Apparatus No. 34:

The apparatus of Exemplary Apparatus No. 33, wherein the backfill data is displayed, when an indication of consent is received.

Exemplary Apparatus No. 35:

The apparatus of any of Exemplary Apparatus Nos. 21 through 34, further comprising: inhibiting, at the apparatus, the receiving of the backfill data, without an indication of consent.

Exemplary Apparatus No. 36:

The apparatus of any of Exemplary Apparatus Nos. 21 through 35, wherein the receiving is in response to a request from the apparatus.

Exemplary Apparatus No. 37:

The apparatus of any of Exemplary Apparatus Nos. 21 through 36, further comprising: classifying, at the apparatus, an alert as a missed alert, when the alert occurred during a time associated with the backfill data.

Exemplary Apparatus No. 38:

The apparatus of any of Exemplary Apparatus Nos. 21 through 37, wherein the backfill data is received as compressed data.

Exemplary Apparatus No. 39:

The apparatus of Exemplary Apparatus No. 38, wherein the compressed data comprises a function representative of at least a portion of a curve corresponding to the backfill data.

Exemplary Apparatus No. 40:

The apparatus of any of Exemplary Apparatus Nos. 21 through 39, wherein the receiving comprises: receiving, at the apparatus, more recent backfill data is received more frequently, when compared to older backfill data.

Exemplary Apparatus No. 41:

The apparatus of any of Exemplary Apparatus Nos. 21 through 40, wherein the apparatus comprises a receiver.

Exemplary Storage Medium No. 42:

A non-transitory computer-readable storage medium including program code which when executed by at least one processor causes operations comprising: receiving, at the apparatus, backfill data representative of sensor data stored, at continuous blood glucose sensor and transmitter assembly, due to a loss of a wireless link between the apparatus and the continuous blood glucose sensor and transmitter assembly; generating, at the apparatus, at least one of a notification or a graphically distinct indicator for presentation at a display of the apparatus, the at least one of the notification or the graphically distinct indicator enabling the backfill data to be graphically distinguished, when presented at the display, from non-backfill data; and generating, at the apparatus, a view including the backfill data, the non-backfill data, and the generated at least one of the notification or the graphically distinct indicator.

Exemplary Apparatus No. 43:

An apparatus comprising: means for receiving backfill data representative of sensor data stored, at continuous blood glucose sensor and transmitter assembly, due to a loss of a wireless link between the apparatus and the continuous blood glucose sensor and transmitter assembly; means for generating at least one of a notification or a graphically distinct indicator for presentation at a display of the apparatus, the at least one of the notification or the graphically distinct indicator enabling the backfill data to be graphically distinguished, when presented at the display, from non-backfill data; and means for generating a view including the backfill data, the non-backfill data, and the generated at least one of the notification or the graphically distinct indicator.

Exemplary Apparatus No. 44:

The apparatus of Exemplary Apparatus No. 43, further comprising means for performing any of Exemplary Method Nos. 2 through 20.

Exemplary Apparatus No. 45:

The apparatus of any of Exemplary Apparatus Nos. 43 through 44, wherein the apparatus comprises a receiver.

Exemplary Method No. 46:

A method comprising: transmitting, by an analyte sensor system, at least one advertisement at a first time; receiving, at the analyte sensor system, a data connection request from a user equipment at a second time; establishing, by the analyte sensor system, the data connection with the user equipment; transmitting, by the analyte sensor system, an analyte value to the user equipment; storing, at the analyte sensor system, analyte data as backfill data, when an error occurs in the transmitting the at least one advertisement, the establishing the data connection, and/or the transmitting the analyte value; and transmitting, by the analyte sensor system, the stored backfill data.

Exemplary Method No. 47:

The method of Exemplary Method No. 46, wherein the stored backfill data is transmitted, when another data connection is established to the user equipment.

Exemplary Method No. 48:

The method of any of Exemplary Method Nos. 46 through 47, wherein the stored backfill data is transmitted via one or more other advertisements.

Exemplary Method No. 49:

The method of any of Exemplary Method Nos. 46 through 48, further comprising: performing, before the establishing of the data connection and/or the other data connection, an authentication.

Exemplary Method No. 50:

The method of any of Exemplary Method Nos. 46 through 49, further comprising: storing, at the analyte sensor system, analyte data as backfill data, when an error occurs in the authenticating.

Exemplary Method No. 51:

The method of any of Exemplary Method Nos. 46 through 50, wherein the error represents a state in which the transmitting the at least one advertisement, the establishing the data connection, the transmitting the analyte value, and/or the authenticating are not successful.

Exemplary Method No. 52:

The method of any of Exemplary Method Nos. 46 through 51, wherein the user equipment comprises a mobile wireless device, a smart phone, a tablet, and/or a display device.

Exemplary Apparatus No. 53:

An apparatus comprising: at least one processor; and at least one memory including computer program code which when executed causes operations comprising: transmitting, by the apparatus, at least one advertisement at a first time; receiving, at the apparatus, a data connection request from a user equipment at a second time; establishing, by the apparatus, the data connection with the user equipment; transmitting, by the apparatus, an analyte value to the user equipment; storing, at the apparatus, analyte data as backfill data, when an error occurs in the transmitting the at least one advertisement, the establishing the data connection, and/or the transmitting the analyte value; and transmitting, by the apparatus, the stored backfill data.

Exemplary Apparatus No. 54:

The apparatus of Exemplary Apparatus No. 53, wherein the stored backfill data is transmitted, when another data connection is established to the user equipment.

Exemplary Apparatus No. 55:

The apparatus of any of Exemplary Apparatus Nos. 53 through 54, wherein the stored backfill data is transmitted via one or more other advertisements.

Exemplary Apparatus No. 56: The apparatus of any of Exemplary Apparatus Nos. 53 through 55, further comprising: performing, before the establishing of the data connection and/or the other data connection, an authentication.

Exemplary Apparatus No. 57:

The apparatus of any of Exemplary Apparatus Nos. 53 through 56, further comprising: storing, at the apparatus, analyte data as backfill data, when an error occurs in the authenticating.

Exemplary Apparatus No. 58:

The apparatus of any of Exemplary Apparatus Nos. 53 through 57, wherein the error represents a state in which the transmitting the at least one advertisement, the establishing the data connection, the transmitting the analyte value, and/or the authenticating are not successful.

Exemplary Apparatus No. 59:

The apparatus of any of Exemplary Apparatus Nos. 53 through 58, wherein the user equipment comprises a mobile wireless device, a smart phone, a tablet, and/or a display device.

Exemplary Apparatus No. 66:

The apparatus of any of Exemplary Apparatus Nos. 53 through 59, wherein the apparatus comprises an analyte sensor system.

Exemplary Storage Medium No. 61:

A non-transitory computer-readable storage medium including program code which when executed by at least one processor causes operations comprising: transmitting, by the apparatus, at least one advertisement at a first time; receiving, at the apparatus, a data connection request from a user equipment at a second time; establishing, by the apparatus, the data connection with the user equipment; transmitting, by the apparatus, an analyte value to the user equipment; storing, at the apparatus, analyte data as backfill data, when an error occurs in the transmitting the at least one advertisement, the establishing the data connection, and/or the transmitting the analyte value; and transmitting, by the apparatus, the stored backfill data.

Exemplary Apparatus No. 62:

An apparatus comprising: means for transmitting, by the apparatus, at least one advertisement at a first time; means for receiving, at the apparatus, a data connection request from a user equipment at a second time; means for establishing, by the apparatus, the data connection with the user equipment; means for transmitting, by the apparatus, an analyte value to the user equipment; means for storing, at the apparatus, analyte data as backfill data, when an error occurs in the transmitting the at least one advertisement, the establishing the data connection, and/or the transmitting the analyte value; and means for transmitting, by the apparatus, the stored backfill data.

Exemplary Apparatus No. 63:

The apparatus of Exemplary Apparatus No. 62, further comprising means for performing any of Exemplary Method Nos. 47 through 52.

Exemplary Apparatus No. 64:

The apparatus of any of Exemplary Apparatus Nos. 62 through 63, wherein the apparatus comprises an analyte sensor system.

Exemplary Method No. 65:

A method comprising: receiving, by a user equipment, at least one advertisement at a first time from an analyte sensor system: transmitting, by the user equipment, a data connection request to the analyte sensor system at a second time; establishing the data connection with the analyte sensor system; receiving, by the user equipment, an analyte value from the analyte sensor system; and receiving, by the user equipment, backfill data stored at the analyte sensor system, when an error occurs.

Exemplary Method No. 66:

The method of Exemplary Method No. 65, wherein the stored backfill data is received, when another data connection is established.

Exemplary Method No. 67:

The method of any of Exemplary Method Nos. 65 through 66, wherein the stored backfill data is received via one or more other advertisements.

Exemplary Method No. 68:

The method of any of Exemplary Method Nos. 65 through 67, further comprising: performing, before the establishing of a data connection, an authentication.

Exemplary Method No. 69:

The method of any of Exemplary Method Nos. 65 through 68, wherein the error represents a state in which the receiving the at least one advertisement, the transmitting the data connection request, the establishing the data connection, the receiving the analyte value, and/or the authentication are not successful.

Exemplary Method No. 70:

The method of any of Exemplary Method Nos. 65 through 69, wherein the user equipment comprises a mobile wireless device, a smart phone, a tablet, and/or a display device.

Exemplary Apparatus No. 71:

An apparatus comprising: at least one processor; and at least one memory including computer program code which when executed causes operations comprising: receiving, by the apparatus, at least one advertisement at a first time from an analyte sensor system; transmitting, by the apparatus, a data connection request to the analyte sensor system at a second time; establishing the data connection with the analyte sensor system; receiving, by the apparatus, an analyte value from the analyte sensor system; and receiving, by the apparatus, backfill data stored at the analyte sensor system, when an error occurs.

Exemplary Apparatus No. 72:

The apparatus of Exemplary Apparatus No. 71, wherein the stored backfill data is received, when another data connection is established.

Exemplary Apparatus No. 73:

The apparatus of any of Exemplary Apparatus Nos. 71 through 72, wherein the stored backfill data is received via one or more other advertisements.

Exemplary Apparatus No. 74:

The apparatus of any of Exemplary Apparatus Nos. 71 through 73, further comprising: performing, before the establishing of a data connection, an authentication.

Exemplary Apparatus No. 75:

The apparatus of any of Exemplary Apparatus Nos. 71 through 74, wherein the error represents a state in which the receiving the at least one advertisement, the transmitting the data connection request, the establishing the data connection, the receiving the analyte value, and/or the authentication are not successful.

Exemplary Apparatus No. 76:

The apparatus of any of Exemplary Apparatus Nos. 71 through 75, wherein the apparatus comprises a mobile wireless device, a smart phone, a tablet, and/or a display device.

Exemplary Storage Medium No. 77:

A non-transitory computer-readable storage medium including program code which when executed by at least one processor causes operations comprising: receiving, by a user equipment, at least one advertisement at a first time from an analyte sensor system; transmitting, by the user equipment, a data connection request to the analyte sensor system at a second time; establishing the data connection with the analyte sensor system; receiving, by the user equipment, an analyte value from the analyte sensor system; and receiving, by the user equipment, backfill data stored at the analyte sensor system, when an error occurs.

Exemplary Apparatus No. 78:

An apparatus comprising: means for receiving, by the apparatus, at least one advertisement at a first time from an analyte sensor system; means for transmitting, by the apparatus, a data connection request to the analyte sensor system at a second time; means for establishing the data connection with the analyte sensor system; means for receiving, by the apparatus, an analyte value from the analyte sensor system; and means for receiving, by the apparatus, backfill data stored at the analyte sensor system, when an error occurs.

Exemplary Apparatus No. 79:

The apparatus of Exemplary Apparatus No. 78, further comprising means for performing any of Exemplary Method Nos. 66 through 70.

Exemplary Apparatus No. 80:

The apparatus of any of Exemplary Apparatus Nos. 62 through 63, wherein the apparatus comprises a user equipment.

Exemplary Method No. 81:

A method comprising: transmitting, by a user equipment, a data connection request to the analyte sensor system; establishing the data connection with the analyte sensor system; checking, by the user equipment, for private data stored at the user equipment and associated with the analyte sensor system, the private data encrypted to inhibit access by the user equipment; when the checking identifies private data associated with the analyte sensor system, requesting private data from the analyte sensor system; when the checking does not identify private data associated with the analyte sensor system, requesting, from the analyte sensor system, manifest data for the private data, and requesting, in response to receiving the manifest data, private data from the analyte sensor system; and receiving the requested private data to enable storage before forwarding to a server.

Exemplary Method No. 82:

The method of Exemplary Method No. 81, wherein the checking further comprises: querying a database to determine whether there is private data stored for the analyte sensor system.

Exemplary Method No. 83:

The method of any of Exemplary Method Nos. 81 through 82, wherein the requesting for private data further comprises a time frame over which the private data is requested.

Exemplary Method No. 84:

The method of Exemplary Method No. 83, wherein the time frame is determined based on a time stamp obtained from private data stored in the database.

Exemplary Method No. 85:

The method of any of Exemplary Method Nos. 81 through 84, wherein the manifest data describes the private data.

Exemplary Method No. 86:

The method of any of Exemplary Method Nos. 81 through 85, wherein the user equipment comprises a mobile wireless device, a smart phone, a tablet, and/or a display device.

Exemplary Apparatus No. 87:

An apparatus comprising: at least one processor; and at least one memory including computer program code which when executed causes operations comprising: transmitting, by the apparatus, a data connection request to the analyte sensor system; establishing the data connection with the analyte sensor system; checking, by the apparatus, for private data stored at the apparatus and associated with the analyte sensor system, the private data encrypted to inhibit access by the apparatus; when the checking identifies private data associated with the analyte sensor system, requesting private data from the analyte sensor system; when the checking does not identify private data associated with the analyte sensor system, requesting, from the analyte sensor system, manifest data for the private data, and requesting, in response to receiving the manifest data, private data from the analyte sensor system; and receiving the requested private data to enable storage before forwarding to a server.

Exemplary Apparatus No. 88:

The apparatus of Exemplary Apparatus No. 87, wherein the checking further comprises: querying a database to determine whether there is private data stored for the analyte sensor system.

Exemplary Apparatus No. 89:

The apparatus of any of Exemplary Apparatus Nos. 87 through 88, wherein the requesting for private data further comprises a time frame over which the private data is requested.

Exemplary Apparatus No. 90:

The apparatus of Exemplary Apparatus No. 89, wherein the time frame is determined based on a time stamp obtained from private data stored in the database.

Exemplary Apparatus No. 91:

The apparatus of any of Exemplary Apparatus Nos. 87 through 90, wherein the manifest data describes the private data.

Exemplary Apparatus No. 92:

The apparatus of any of Exemplary Apparatus Nos. 87 through 91, wherein the apparatus comprises a user equipment, wherein the user equipment comprises a mobile wireless device, a smart phone, a tablet, and/or a display device.

Exemplary Storage Medium No. 93:

A non-transitory computer-readable storage medium including program code which when executed by at least one processor causes operations comprising: transmitting, by a user equipment, a data connection request to the analyte sensor system; establishing the data connection with the analyte sensor system; checking, by the user equipment, for private data stored at the user equipment and associated with the analyte sensor system, the private data data encrypted to inhibit access by the user equipment; when the checking identifies private data associated with the analyte sensor system, requesting private data from the analyte sensor system; when the checking does not identify private data associated with the analyte sensor system, requesting, from the analyte sensor system, manifest data for the private data, and requesting, in response to receiving the manifest data, private data from the analyte sensor system; and receiving the requested private data to enable storage before forwarding to a server.

Exemplary Apparatus No. 94:

An apparatus comprising: means for transmitting, by the apparatus, a data connection request to the analyte sensor system; means for establishing the data connection with the analyte sensor system; means for checking, by the apparatus, for private data stored at the apparatus and associated with the analyte sensor system, the private data encrypted to inhibit access by the apparatus; when the checking identifies private data associated with the analyte sensor system, means for requesting private data from the analyte sensor system; when the checking does not identify private data associated with the analyte sensor system, means for requesting, from the analyte sensor system, manifest data for the private data, and means for requesting, in response to receiving the manifest data, private data from the analyte sensor system, and means for receiving the requested private data to enable storage before forwarding to a server.

Exemplary Apparatus No. 95:

An apparatus further comprising means for performing any of Exemplary Method Nos. 82 through 86.

Exemplary Apparatus No. 96:

The apparatus of any of Exemplary Apparatus Nos. 94 through 95, wherein the apparatus comprises a user equipment.

Various implementations of the subject matter described herein may be realized in digital electronic circuitry, integrated circuitry, specially designed ASICs (application specific integrated circuits), computer hardware, firmware, software, and/or combinations thereof. The circuitry may be affixed to a printed circuit board (PCB), or the like, and may take a variety of forms, as noted. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, audible feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

Although a few variations have been described in detail above, other modifications are possible. For example, while the descriptions of specific implementations of the current subject matter discuss analytic applications, the current subject matter is applicable to other types of software and data services access as well. Moreover, although the above description refers to specific products, other products may be used as well. In addition, the logic flows depicted in the accompanying figures and described herein do not require the particular order shown, or sequential order, to achieve desirable results. Other implementations may be within the scope of the following claims.

What is claimed is:

1. A method comprising:
   transmitting, by a user equipment, a data connection request to the analyte sensor system;
   establishing the data connection with the analyte sensor system;
   checking, by the user equipment, for private data stored at the user equipment and associated with the analyte sensor system, the private data encrypted to inhibit access by the user equipment;
   when the checking identifies private data associated with the analyte sensor system, requesting private data from the analyte sensor system;
   when the checking does not identify private data associated with the analyte sensor system,
      requesting, from the analyte sensor system, manifest data for the private data, and
      requesting, in response to receiving the manifest data, private data from the analyte sensor system; and
      receiving the requested private data to enable storage before forwarding to a server.

2. The method of claim 1, wherein the checking further comprises:
   querying a database to determine whether there is private data stored for the analyte sensor system.

3. The method of claim 1, wherein the requesting for private data further comprises a time frame over which the private data is requested.

4. The method of claim 3, wherein the time frame is determined based on a time stamp obtained from private data stored in the database.

5. The method of claim 1, wherein the manifest data describes the private data.

6. The method of claim 1, wherein the user equipment comprises a mobile wireless device, a smart phone, a tablet, and/or a display device.

7. An apparatus comprising:
   at least one processor; and
   at least one memory including computer program code which when executed causes operations comprising:
   transmitting, by the apparatus, a data connection request to the analyte sensor system;
   establishing the data connection with the analyte sensor system;
   checking, by the apparatus, for private data stored at the apparatus and associated with the analyte sensor system, the private data encrypted to inhibit access by the apparatus;
   when the checking identifies private data associated with the analyte sensor system, requesting private data from the analyte sensor system;
   when the checking does not identify private data associated with the analyte sensor system,
      requesting, from the analyte sensor system, manifest data for the private data, and
      requesting, in response to receiving the manifest data, private data from the analyte sensor system; and
      receiving the requested private data to enable storage before forwarding to a server.

8. The apparatus of claim 7, wherein the checking further comprises:
   querying a database to determine whether there is private data stored for the analyte sensor system.

9. The apparatus of claim 7, wherein the requesting for private data further comprises a time frame over which the private data is requested.

10. The apparatus of claim 9, wherein the time frame is determined based on a time stamp obtained from private data stored in the database.

11. The apparatus of claim 7, wherein the manifest data describes the private data.

12. The apparatus of claim 7, wherein the apparatus comprises a user equipment, wherein the user equipment comprises a mobile wireless device, a smart phone, a tablet, and/or a display device.

13. A non-transitory computer-readable storage medium including program code which when executed by at least one processor causes operations comprising:

transmitting, by a user equipment, a data connection request to the analyte sensor system;

establishing the data connection with the analyte sensor system;

checking, by the user equipment, for private data stored at the user equipment and associated with the analyte sensor system, the private data data encrypted to inhibit access by the user equipment;

when the checking identifies private data associated with the analyte sensor system, requesting private data from the analyte sensor system;

when the checking does not identify private data associated with the analyte sensor system, requesting, from the analyte sensor system, manifest data for the private data, and requesting, in response to receiving the manifest data, private data from the analyte sensor system; and receiving the requested private data to enable storage before forwarding to a server.

\* \* \* \* \*

UNITED STATES PATENT AND TRADEMARK OFFICE
CERTIFICATE OF CORRECTION

PATENT NO. : 10,169,539 B2
APPLICATION NO. : 15/287581
DATED : January 1, 2019
INVENTOR(S) : Eli Reihman Page 1 of 2

It is certified that error appears in the above-identified patent and that said Letters Patent is hereby corrected as shown below:

On the Title Page

Column 2, item (56), U.S. Patent Documents, Line 1, delete "Label" and insert -- Lebel --.

In the Specification

In Column 10, Line 22, delete "computer readable" and insert -- computer-readable --.

In Column 16, Line 4, delete "value)" and insert -- value --.

In Column 16, Line 33, delete "1258" and insert -- 12:58 --.

In Column 17, Line 49, delete "hypoglycemic," and insert -- hypo-glycemic, --.

In Column 24, Line 13, delete "Ti a" and insert -- Tinterval --.

In Column 29, Line 32, delete "an a" and insert -- a --.

In Column 30, Line 25, delete "110-113)" and insert -- 110-113 --.

In Column 30, Line 39, delete "TransmitterEncyrptionInfo" and insert -- TransmitterEncryptionInfo --.

In Column 30, Line 46, delete "InRangelnclusive" and insert -- InRangeInclusive --.

In Column 32, Line 10, delete "1" and insert -- 1: --.

In Column 32, Line 25, delete "2" and insert -- 2: --.

In Column 32, Line 30, delete "3" and insert -- 3: --.

Signed and Sealed this
Twenty-first Day of January, 2020

Andrei Iancu
*Director of the United States Patent and Trademark Office*

In Column 32, Line 35, delete "4" and insert -- 4: --.

In Column 32, Line 39, delete "5" and insert -- 5: --.

In Column 32, Line 43, delete "6" and insert -- 6: --.

In Column 32, Line 47, delete "7" and insert -- 7: --.

In Column 32, Line 51, delete "8" and insert -- 8: --.

In Column 32, Line 55, delete "9" and insert -- 9: --.

In Column 32, Line 59, delete "10" and insert -- 10: --.

In Column 32, Line 64, delete "11" and insert -- 11: --.

In Column 33, Line 1, delete "12" and insert -- 12: --.

In Column 33, Line 5, delete "13" and insert -- 13: --.

In Column 33, Line 11, delete "14" and insert -- 14: --.

In Column 33, Line 15, delete "15" and insert -- 15: --.

In Column 33, Line 20, delete "16" and insert -- 16: --.

In Column 33, Line 24, delete "17" and insert -- 17: --.

In Column 33, Line 29, delete "18" and insert -- 18: --.

In Column 33, Line 32, delete "19" and insert -- 19: --.

In Column 33, Line 36, delete "20" and insert -- 20: --.

In Column 33, Line 41, delete "21" and insert -- 21: --.

In Column 37, Line 52, delete "system:" and insert -- system; --.

In Column 40, Line 37, delete "data data" and insert -- data --.

In Column 40, Line 63, delete "system," and insert -- system; --.

In the Claims

In Column 44, Line 5, Claim 13, delete "data data" and insert -- data --.